US008809261B2

(12) United States Patent
Elsohly et al.

(10) Patent No.: US 8,809,261 B2
(45) Date of Patent: Aug. 19, 2014

(54) COMPOSITIONS CONTAINING DELTA-9-THC-AMINO ACID ESTERS AND PROCESS OF PREPARATION

(75) Inventors: Mahmoud A. Elsohly, Oxford, MS (US); Waseem Gul, Oxford, MS (US); Michael A. Repka, Oxford, MS (US); Soumyajit Majumdar, Oxford, MS (US)

(73) Assignee: Elsohly Laboratories, Incorporated, Oxford, MS (US)

( * ) Notice: Subject to any disclaimer, the term of this patent is extended or adjusted under 35 U.S.C. 154(b) by 0 days.

(21) Appl. No.: 13/126,606

(22) PCT Filed: Nov. 2, 2009

(86) PCT No.: PCT/US2009/062998
§ 371 (c)(1),
(2), (4) Date: Jul. 15, 2011

(87) PCT Pub. No.: WO2010/051541
PCT Pub. Date: May 6, 2010

(65) Prior Publication Data
US 2011/0275555 A1 Nov. 10, 2011

Related U.S. Application Data

(60) Provisional application No. 61/110,165, filed on Oct. 31, 2008.

(51) Int. Cl.
*A61K 38/00* (2006.01)
*A61K 47/00* (2006.01)
*C07D 405/12* (2006.01)
*C07D 311/80* (2006.01)

(52) U.S. Cl.
CPC ............ *C07D 311/80* (2013.01); *C07D 405/12* (2013.01)
USPC ........................................................ 514/1.3

(58) Field of Classification Search
CPC ....... A61K 38/04; A61K 38/05; A61K 38/06; C07K 5/0812
See application file for complete search history.

(56) References Cited

U.S. PATENT DOCUMENTS 4,933,363 A 6/1990 ElSohly
5,389,375 A * 2/1995 ElSohly ........................ 424/436

(Continued)

FOREIGN PATENT DOCUMENTS

GB 1 313 977 A 4/1973
JP 2008-522959 A 7/2006

(Continued)

OTHER PUBLICATIONS
Anand, et al. "Novel dipeptide prodrugs of acyclovir for ocular herpes infections: bioreversion, antiviral activity and transport across rabbit cornea." Current Eye Research, Mar. 1, 2003; pp. 151-163; vol. 26, No. 3-04.

(Continued)

*Primary Examiner* — Marcela M Cordero Garcia
*Assistant Examiner* — Sergio Coffa
(74) *Attorney, Agent, or Firm* — Hershkovitz & Associates, PLLC; Abraham Hershkovitz; Eugene Rzucidlo

(57) ABSTRACT

Compositions of the formulae (I), (II) and (III); where R1, R2 and R3 are residues of amino acids such as, but not limited to, valine, sarcosine, leucine, glutamine, tryptophan, tyrosine, alanine and 4(4-aminophenyl)butyric acid or combination thereof, and salts thereof. Methods of preparation of these compositions and methods of treating any disease condition responsive to THC comprising administration of at least one these compositions in a pharmaceutically acceptable carrier using a pharmaceutically acceptable formulation.

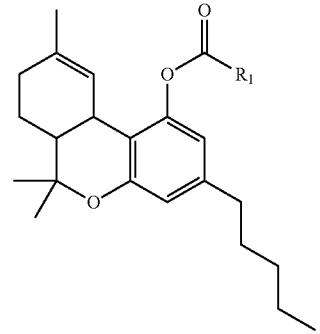

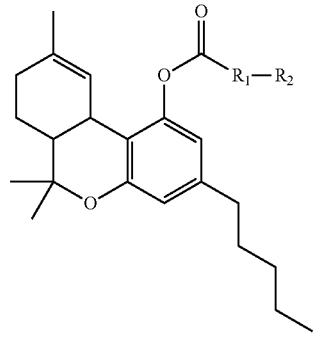

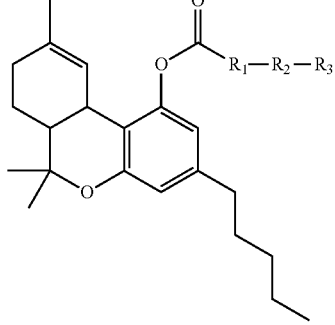

66 Claims, 18 Drawing Sheets

(56) References Cited

U.S. PATENT DOCUMENTS

| | | | |
|---|---|---|---|
| 5,508,037 | A | 4/1996 | ElSohly |
| 6,008,383 | A * | 12/1999 | Elsohly et al. ............ 549/390 |
| 2006/0078955 | A1 | 4/2006 | Lin |
| 2008/0306285 | A1 | 12/2008 | Hale et al. |
| 2009/0143462 | A1 | 6/2009 | Stinchcomb et al. |

FOREIGN PATENT DOCUMENTS

| | | |
|---|---|---|
| WO | WO 2006/050421 A1 | 5/2006 |
| WO | WO 2008/134668 A2 | 11/2008 |
| WO | WO 2009/073633 A1 | 6/2009 |

OTHER PUBLICATIONS

Bundgaard, et al. "Prodrugs as drug delivery systems XXVI. Preparation and enzymatic hydrolysis of various water-soluble amino acid esters of metronidazole." International Journal of Pharmaceutics, Jan. 1, 1984; pp. 67-77; vol. 18, No. 1-2.

Elsohly, et al. "Rectal bioavailability of delta-9-tetrahydrocannabinol from various esters." Pharmacology Biochemistry and Behavior, Nov. 1, 1991; pp. 497-502; vol. 40 No. 3.

Kovach, et al. "Amino acid esters of phenols as prodrugs: Synthesis and stability of glycine, beta-aspartic acid, and alpha-aspartic acid esters of para-acetamidophenol." Journal of Pharmaceutical Sciences, Jan. 1, 1981; pp. 881-885; vol. 70, No. 8.

Senel, et al. "Drug permeation enhancement via buccal route: possibilities and limitations." Journal of Controlled Release, May 14, 2001; pp. 133-144; vol. 72, No. 1-3.

Supplementary European Search Report dated Jun. 20, 2012 mailed in European Patent Application No. 09824226.6, published Aug. 10, 2011.

Zitko, et al. "Water-soluble derivatives of Delta-1-tetrahydrocannabinol." Science, Jan. 1, 1997; pp. 442-444; vol. 177.

International Search Report issued May 3, 2010 corresponding to PCT/US2009/062998.

Theodora W. Greene and Peter G.M. Wuts, Protective Groups in Organic Synthesis, John Wiley & Sons, Inc. (Aug. 16, 1999), Third Edition, pp. 526-528.

Japanese Office Action mailed Jan. 20, 2014, in corresponding Japanese Application No. 2011-534860 (together with an English Translation).

* cited by examiner

COMPOSITIONS CONTAINING DELTA-9-THC-AMINO ACID ESTERS AND PROCESS OF PREPARATION

CROSS-REFERENCE PARAGRAPH

This is a National Stage Application of International Application NO. PCT/US2009/62998, filed on Nov. 2, 2009, which is an International Application of U.S. Provisional Application No. 61/110,165, filed on Oct. 31, 2008, the disclosures of all of which are expressly incorporated by reference herein in their entireties.

FIELD OF INVENTION

The present invention relates to composition containing delta-9-THC-amino acid esters and their process of preparation.

BACKGROUND OF THE INVENTION

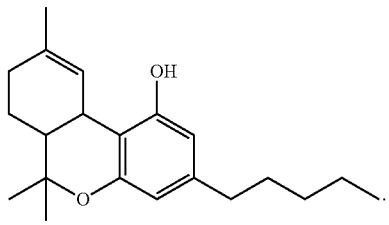

I: Structure of $\Delta^9$- Tetrahydrocannabinol (THC)

$\Delta^9$-Tetrahydrocannabinol (THC, I) is the primary active ingredient of the plant *Cannabis sativa* (marijuana) and is responsible for the majority of the pharmacological effects. People have utilized the plant (that includes numerous cannabinoids) since ancient times for medicinal purposes as well as for its intoxicating properties. While marijuana is primarily known as an abused drug, we believe that there are important pharmacological properties of the active component THC that could be directed to specific therapeutic effects, given the appropriate delivery mechanism. To date, the most promising clinical applications approved by the Food and Drug Administration (FDA) are for the control of nausea and vomiting associated with chemotherapy and for appetite stimulation of AIDS patients suffering from anorexia and wasting syndrome[1, 2].

THC, however, demonstrates other biological activities which lend themselves to possible additional therapeutic applications. These include glaucoma[3], migraine headaches[4, 5] spasticity/epileptic seizures[6, 7], anxiety[8] and chemical dependence withdrawal symptoms. Also, more recently, THC is becoming increasingly recognized as an analgesic[1, 2, 6, 7]. Due to these promising biological activities, THC has potential for multiple medicinal uses.

Challenges in Systemic Delivery of THC:

Parenteral formulations researched include an intramuscular preparation[9] and an intravenous dosage form (neither of which have been approved by FDA). Injectables are inundated with the problems of being invasive and requiring professional assistance, and therefore in many cases preclude self medication. In addition, these parenteral routes are inherently subject to abuse.

Thus, the search for a non-parenteral delivery system for THC continues. The physicochemical characteristics of THC, like many other lipophilic agents, present major challenges to drug delivery scientists. The log P (log octanol/water partition coefficient) value of THC is around 4.0 indicating that it is a highly lipophilic compound. Consequently, THC's solubility in the gastro-intestinal fluids and partitioning from the intestinal membranes into the systemic circulation would be severely limited. Additionally, THC is rapidly metabolized by the hepatic CYP 450 enzymes to the 11-hydroxy metabolite (11-OH-THC), which is responsible for the undesirable side effects of THC[9, 10]. The blood plasma levels desired are in the range of 10 ng/ml—enough to provide a therapeutic effect without the production of a significant "high" (>100 ng/ml)[11, 12]. Poor gastro-intestinal stability of THC further hinders oral absorption. These factors act in conjunction to minimize systemic availability of THC following peroral administration, the most preferred route of administration, and forms the basis of one of the main issues brought into public debate by medicinal marijuana proponents—the fact that the currently available soft gelatin formulation is expensive and lacks consistency in its therapeutic effects and pharmacokinetic profiles. It is significant to note, however, that the only THC dosage form currently approved by FDA is the oral, soft gelatin capsule (Marinol®).

Considering the challenges in intestinal absorption and metabolism, attempts have been made to deliver THC through nasal as well as inhalation routes[13-15]. In a recent phase I pharmacokinetic study[16] performed by GW Pharmaceuticals, UK, Cannabis-based extracts were tested by three different routes of administration via; sublingual, buccal and oropharyngeal. The formulation was administered in the form of sublingual drops as well as a pump action sublingual spray (PASS). In this study, it was reported that buccal administration of the PASS test treatment resulted in a later $T_{max}$ but greater $C_{max}$ when compared to the sublingual and oropharyngeal routes. However, AUC was reported to be greatest following the oropharyngeal route. The lower bioavailability (measured in terms of AUC) following buccal administration, as compared to the sublingual and oropharyngeal routes, is most likely related to the difficulty of spraying onto the inside of the cheek and subsequent loss of the spray.

Although promising, the nasal and oropharyngeal routes are burdened with problems. Potential irritation and the irreversible damage to the ciliary action of the nasal cavity from chronic application of nasal dosage forms, and large intra- and inter-subject variability in mucus secretion in the nasal mucosa that could significantly affect drug absorption from this site. Also, the inhalation route of administration possesses high abuse characteristics. In addition, spray formulations of THC have been shown to have a dosage form-related adverse effect of throat irritation[16]. Other non-parenteral routes examined include sublingual[17], rectal[17-20] and vaginal[21].

SUMMARY OF THE INVENTION

This invention comprises compositions containing delta-9-THC-amino acid esters, methods of their preparation and their use in the treatment of diffeent disease conditions.

This invention also describes methods of preparation of delta-9-THC-amino acid esters. The compositions of this invention have not been previously described.

The compounds of this invention represent a class of amino acid esters, one that will improve formulation characteristics and bioavailability of THC.

The amino acid conjugation can yield THC prodrugs that are significantly more hydrophilic and that exhibit greater thermal, chemical and enzymatic stability. These compositions will provide significant treatment options for many disease states known to be ameliorated by THC, including emesis due to chemotherapy, wasting syndrome of HIV patients, multiple sclerosis, glaucoma, spasticity and pain. Administered in the proper formulation, these compositions will decrease the adverse effects of THC therapy (i.e. diminish the levels of the 11-OH-THC metabolite).

DESCRIPTION OF THE INVENTION

THC-amino acid esters as prodrugs for THC were prepared in this invention by coupling of THC with allyl protected different amino acids to generate the THC-allyl protected amino acid esters which on deprotection produced THC-amino acid esters. THC (FIG. 1) is used as the starting material for all THC-amino acid esters.

THC PRODRUGS

Figure 1:
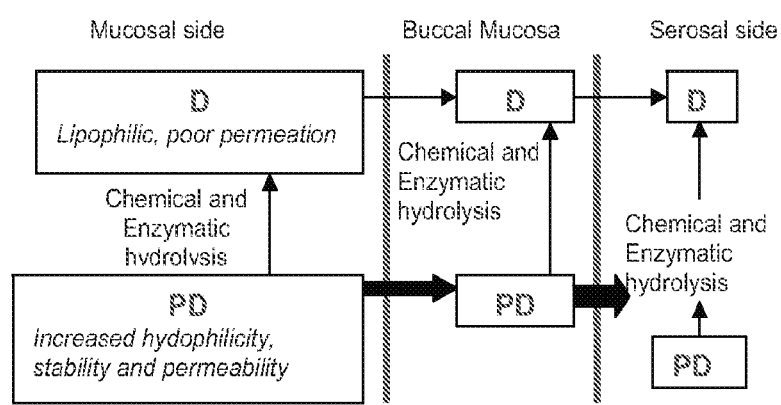
FIG. 1: Schematic representation of the utility of the prodrug/TMP system concept. Prodrug (PD) derivatization of the parent drug THC (D), in combination with the TMP system improves overall permeability. Transbuccal permeability and bioreversion are illustrated by arrows. Line thickness represents the extent and higher or lower rates of permeability.

Chemical modification of a therapeutic agent by way of prodrug design has become an important drug delivery tool[22-24]. This is one of the most widely accepted and successful strategies for modifying physicochemical characteristics, aqueous solubility, chemical and enzymatic stability and mucosal permeability of drug candidates through linkage of appropriate promoieties. A significant positive aspect of the prodrug approach is that it does not induce any change in the membrane structure, fluidity or characteristics. The prodrugs are cleaved in vivo to generate the active drug and the harmless pro-moiety, which is eliminated from the body (FIG. 1).

Amino Acid Prodrugs:

In the past decade amino acids have taken center stage as promoieties for transporter targeted prodrug derivatization of hydrophilic drug molecules[25-31]. Some studies exploiting this mechanism for circumvention of efflux proteins have also been published[32-35]. A few studies exploring the use of single amino acid based prodrug derivatization to enhance hydrophilicity of lipophilic molecules and improve oral absorption have also been reported[28, 36-46]. However, to date, transbuccal delivery of mono-, di- or tri-amino acid conjugated prodrugs of lipophilic compounds has not been investigated. Indeed, a major gap in the understanding of the structural and physicochemical characteristics of any molecule necessary for transbuccal penetration exists. This route of administration holds tremendous untapped potential for the delivery of many therapeutic agents with limited permeability and metabolic stability. Compounds whose systemic bioavailability is limited by hepatic metabolism, as in the case of THC, will necessitate preparation of more permeable prodrugs, such as the mono-, di- and tri-amino acid esters to be formulated in non-oral formulations such as the Transmucosal Matrix Patch (TMP) system with a multitude of advantages. However, the above-cited prodrugs could also be incorporated into an oral delivery system and other compositions using processing techniques, including, but not limited to, hot-melt extrusion to enhance bioavailability. The highlight of this invention is the ability, for the first time, to prepare amino acid esters of THC, without affecting the basic structure of THC.

Increasing the bioavailability of THC, through the use of the amino acid esters prodrugs and incorporating these prodrugs in a formulation such as the Transmucosal Matrix Patch (TMP), or a more efficient oral delivery system, could have a significant influence on many chronically ill patients, such as those infected with the HIV virus, those undergoing chemotherapy, as well as other conditions known to be ameliorated by THC, such as pain, spasticity and multiple sclerosis.

The pharmacologically acceptable compounds of the present invention can be used, for example, for the manufacture of pharmaceutical compositions useful in treatment of chronic states treatable with THC and which contain an effective amount of the active substance together or in admixture with inorganic or organic, solid or liquid, pharmaceutically acceptable carriers.

The pharmaceutical compositions according to the invention are those which are suitable for enteral, such as oral, administration and for parenteral, such as subcutaneous, administration to warm-blooded animals, especially humans, and which contain the pharmacologically active substance on its own or together with a pharmaceutically acceptable carrier. A preferred method of use for the present compositions is by transmucosal patch. The dosage of the active substance depends on the species of warm-blooded animal and on the age and individual condition the illness to be treated and also on the mode of administration.

THC-Amino Acid Prodrugs:

Computational analysis of the amino acid based THC prodrugs: Based on the previous findings, computational analysis, using Molecular modeling Pro® software, was utilized to predict the physicochemical properties of various promoiety candidates.

Computational analysis was subsequently performed with some of the amino acids classified under the hydrophobic amino acid group (e.g. alanine, leucine, valine), as well as with the hydrophilic amino acids (e.g. glycine, serine, sarcosine, esparto acid, tyrosine and glutamine), and their combinations. These results are depicted in Table 1.

TABLE 1

Computed physicochemical properties of select amino acid ester prodrugs of THC. Molecular modeling Pro Software was used for this purpose.

| Sr. No. | Compound | Molecular weight | Molecular formula | mLogP | % hydrophilic surface area | Polar surface area |
|---|---|---|---|---|---|---|
| 1 | THC | 314.46 | $C_{21}H_{30}O_2$ | 3.963 | 5.742 | 29.46 |
| 2 | THC-Ala | 385.54 | $C_{24}H_{35}NO_3$ | 2.438 | 13.163 | 64.71 |
| 3 | THC-Leu | 427.61 | $C_{27}H_{41}NO_3$ | 3.051 | 11.465 | 64.71 |
| 4 | THC-Val | 413.59 | $C_{26}H_{39}NO_3$ | 2.850 | 11.889 | 64.71 |
| 5 | THC-Gly | 371.25 | $C_{23}H_{33}NO_3$ | 2.227 | 16.702 | 64.71 |
| 6 | THC-Ser | 401.54 | $C_{24}H_{35}NO_4$ | 3.183 | 22.742 | 84.94 |
| 7 | THC-Sar | 385.26 | $C_{24}H_{35}NO_3$ | 2.438 | 21.070 | 50.72 |
| 8 | THC-Asp | 429.55 | $C_{25}H_{35}NO_5$ | 3.286 | 21.844 | 105.17 |
| 9 | THC-Tyr | 477.63 | $C_{30}H_{39}NO_4$ | 2.683 | 16.064 | 84.94 |
| 10 | THC-Tyr-Gln | 605.8 | $C_{35}H_{47}N_3O_6$ | 4.27 | 28.687 | 163.45 |
| 11 | THC-Tyr-(Gln)$_2$ | 733.9 | $C_{40}H_{55}N_5O_8$ | 3.32 | 35.529 | 244.95 |
| 12 | THC-Gln | 442.28 | $C_{26}H_{38}N_2O_4$ | 2.36 | 22.833 | 110.96 |
| 13 | THC-Gln-Val | 541.35 | $C_{31}H_{47}N_3O_5$ | 4.95 | 25.434 | 143.22 |
| 14 | THC-Gln-Val-Val | 640.42 | $C_{36}H_{56}N_4O_6$ | 5.98 | 27.886 | 175.48 |
| 15 | THC-Val-Gly | 470.64 | $C_{28}H_{42}N_2O_4$ | 4.296 | 20.319 | 96.97 |
| 16 | THC-Val-Gly-Gly | 527.70 | $C_{30}H_{45}N_3O_5$ | 5.782 | 27.276 | 129.23 |

The results predict a significant decrease in the log P values and increase in hydrophilicity with both hydrophilic and hydrophobic amino acid prodrugs evaluated. The polar surface area and the % hydrophilic surface area are also significantly improved. Additionally the di- and tri-amino acid (peptide) linkages will allow significant modulation of the physicochemical properties. Thus depending on the type of amino acid selected and the number of amino acids linked to THC, a wide range of hydrophilicities can be generated and permeabilities determined. Thus the correlation of log P and permeability can be determined.

THC-Amino Acid Esters Synthesis:

Several procedures were attempted for the preparation of the $\Delta^9$-THC amino acid derivatives using the t-boc and F-moc protected amino acids. While the formation of the esters with the protected amino groups was not problematic for all of the amino acid derivatives attempted, deprotection of the t-boc or the F-moc groups under various deprotection conditions always resulted in conversion of the $\Delta^9$-THC (at least in part) to $\Delta^8$-THC, in case of the t-boc, or reversion to $\Delta^9$-THC in the case of the F-moc. In this invention, we have developed allyl protected amino acids prepared in house (scheme I) to overcome the problems associated with the commonly available protected amino acids. This approach proved to be successful and promises viability in the preparation of any amino acid derivative or small chain peptide derivatives of $\Delta^9$-THC without any effect on the rest of the structure. The di-amino acid derivative could be converted to the tri-amino acid derivative following the same procedure as for the conversion of the mono- to the di-derivative.

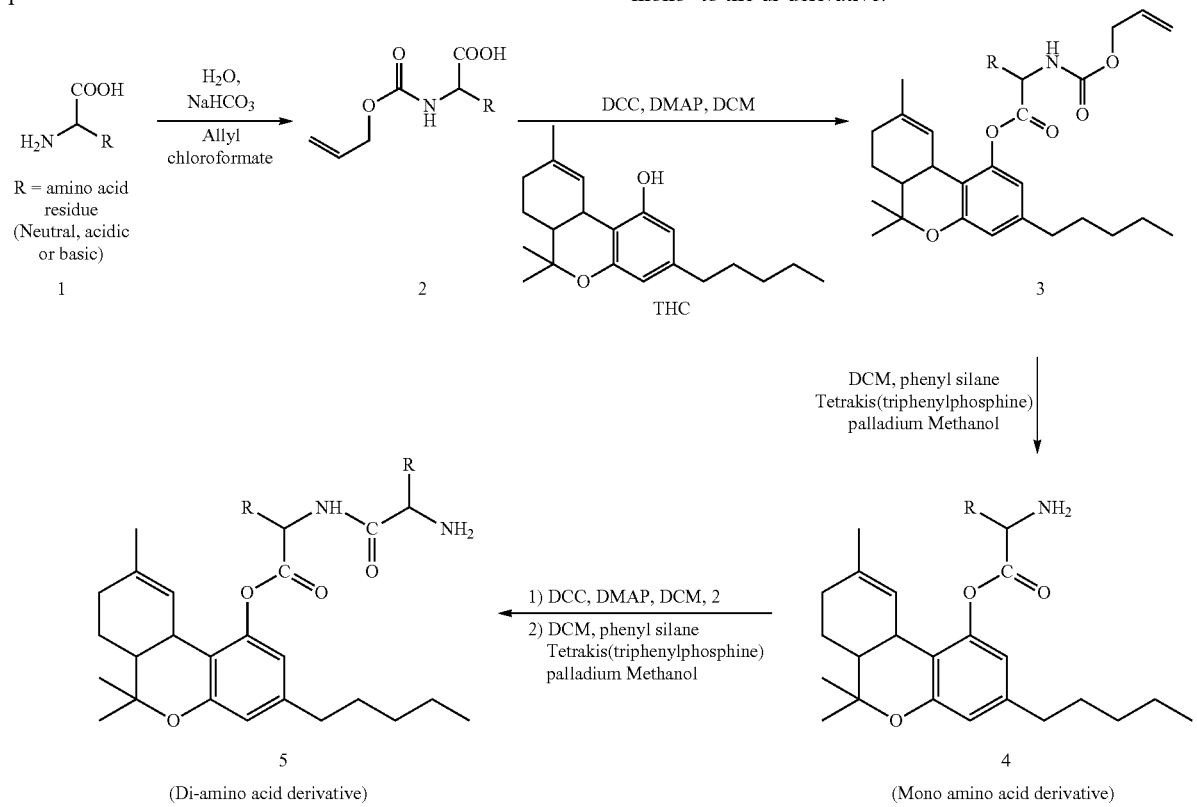

General Scheme for the Preparation of Mono, Di and Tri-Amino Acid Thc Derivatives. Scheme I.

Examples of amino acid esters prepared according to scheme I, are: $\Delta^9$-THC-valinate (6), THC-sarcosinate (7), THC-leucinate (8), THC-glutaminate (9) THC-tryptophinate (10), THC-tyrosinate (11) and THC-B-alaninate (12) were prepared. The compounds THC-4-(4-amino-phenyl)butyrate) (13), and THC-4-(4-amino-phenyl)butyrate)hemisuccinate (14) and THC-valinate-hemisuccinate (15) were prepared using scheme II.

Their structures were confirmed by mass (LC/MS and HREIMS) and spectroscopic analysis ($^1$H-NMR and $^{13}$C-NMR).

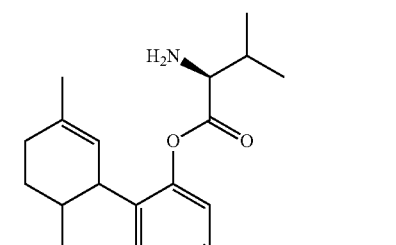

Chemical Formula: $C_{26}H_{39}NO_3$
Molecular Weight: 413.5928
THC-valinate (6)

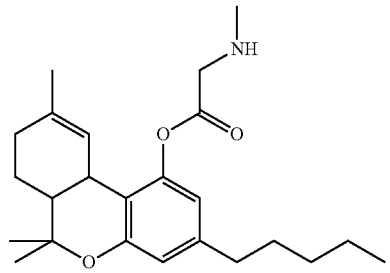

Chemical Formula: $C_{24}H_{35}NO_3$
Molecular Weight: 385.5396
THC-sarcosinate (7)

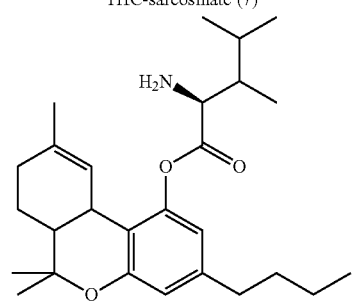

Chemical Formula: $C_{26}H_{39}NO_3$
Molecular Weight: 413.5928
THC-leucinate (8)

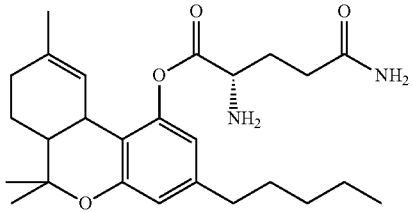

Chemical Formula: $C_{26}H_{38}N_2O_4$
Molecular Weight: 442.5909
THC-glutaminate (9)

-continued

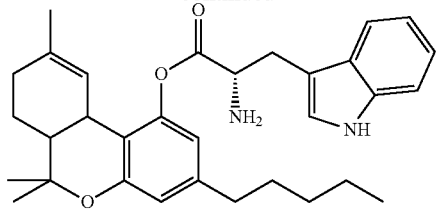

Chemical Formula: $C_{32}H_{40}N_2O_3$
Molecular Weight: 500.6716
THC-tryptophanate (10)

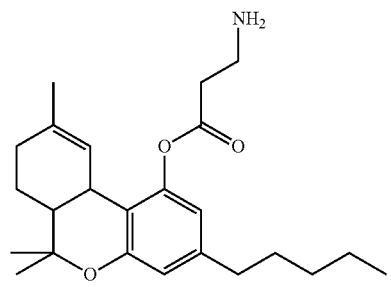

Chemical Formula: $C_{30}H_{39}NO_4$
Molecular Weight: 477.6350
THC-tyrosinate (11)

Chemical Formula: $C_{24}H_{35}NO_3$
Molecular Weight: 385.5396
THC-B-alaninate (12)

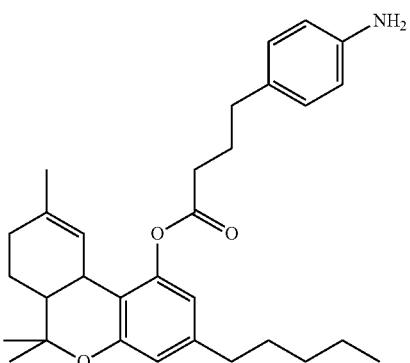

Chemical Formula: $C_{31}H_{41}NO_3$
Molecular Weight: 475.6621
THC-4-(4-amino-phenyl)butyrate (13)

-continued

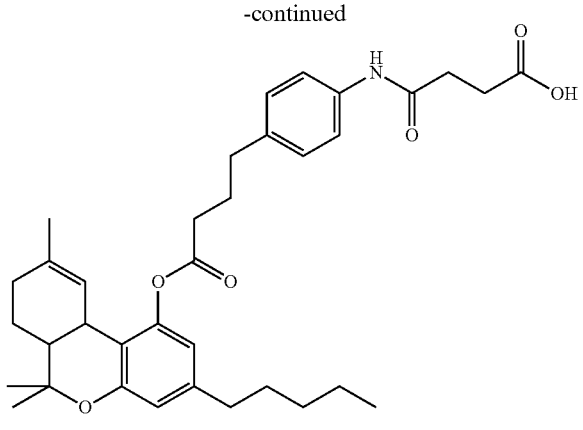

Chemical Formula: $C_{35}H_{45}NO_6$
Molecular Weight: 575.7349
THC-4-(4-amino-phenyl)butyrate hemisuccinate (14)

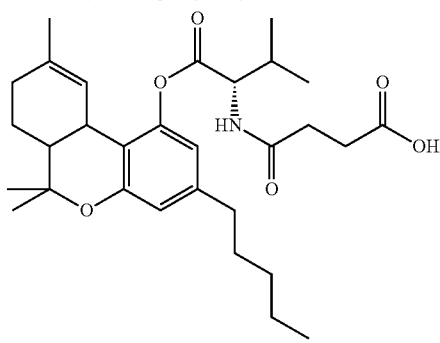

Chemical Formula: $C_{30}H_{43}NO_6$
Molecular Weight: 513.6655
THC-valinate-hemisuccinate (15)

EXAMPLES (COMPOUNDS 6-15)

Example 1

Preparation of $\Delta^9$-THC-valinate (6)

Following the general procedure outlined in Scheme I, where compound 1 is valine, $\Delta^9$-THC-valinate 6 was synthesized to test the validity of the synthetic protocol. Valine (5 g) was dissolved in 34 mL of distilled water and 5.8 gram of sodium carbonate was added in several portions. Allyl chloroformate (10 mL) was added at once after the bubbling stopped. The solution was stirred for 24 hours at 22° C. Concentrated hydrochloric acid was then used to adjust the pH to 1. The solution was extracted with ethyl acetate 8 times and the organic layer was rinsed with brine and dried over sodium sulfate. The solvent was evaporated to dryness to give 6.5 g of the crude product as a colorless syrup.

A 1.1 equivalent of this product was dissolved in dichloromethane and 1.1 equivalent of DCC was added to it (solution A). $\Delta^9$-THC (1 equivalent) was dissolved in dichloromethane along with a catalytic amount of DMAP (dimethyl amino pyridine) which was added drop-wise to solution A. The reaction mixture was stirred at room temperature for 1 hour and the reaction progress was monitored through TLC. After one hour the reaction mixture was worked up and the product was purified using silica gel column chromatography. Fractions having the product were combined and evaporated to obtain the protected $\Delta^9$-THC-valine ester (95% yield), which was confirmed by mass spectroscopy.

Figure 2:
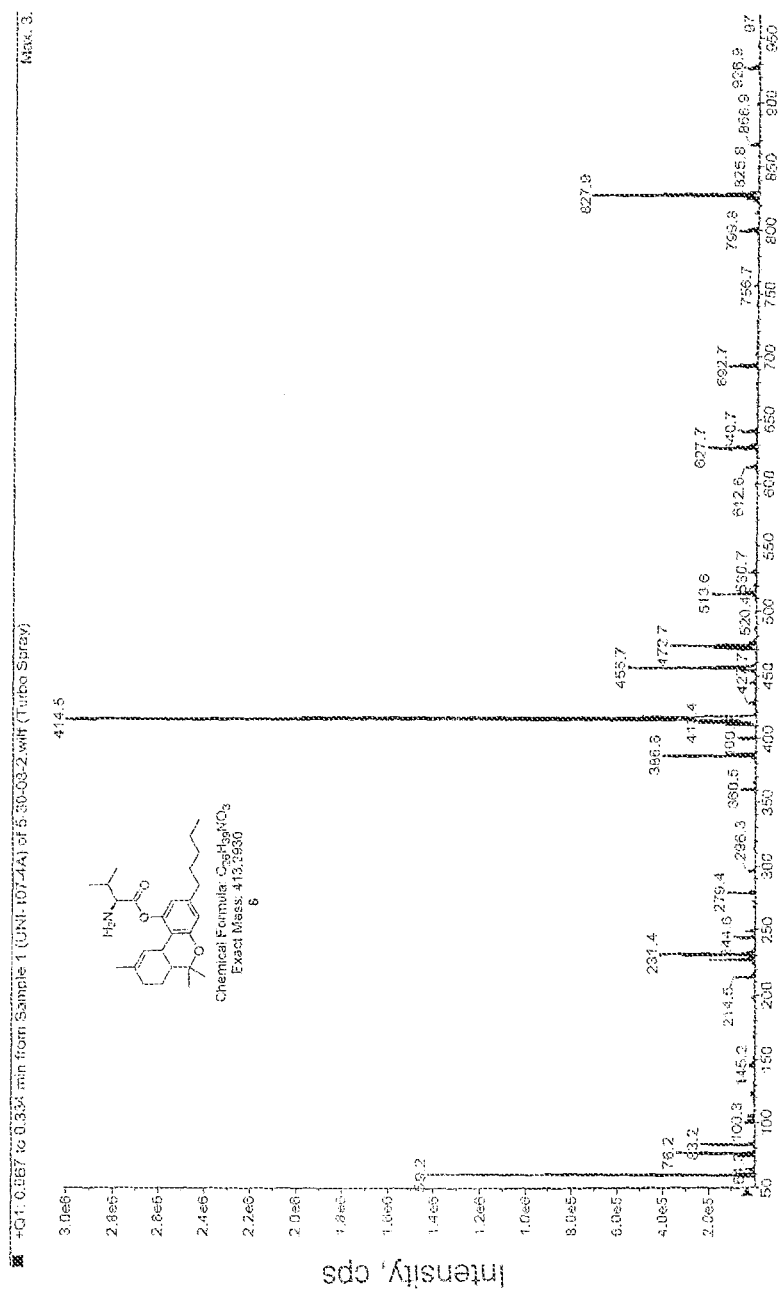
FIG. 2: LC/MS of compound 6 (+ive mode) M+H=414
Figure 3:
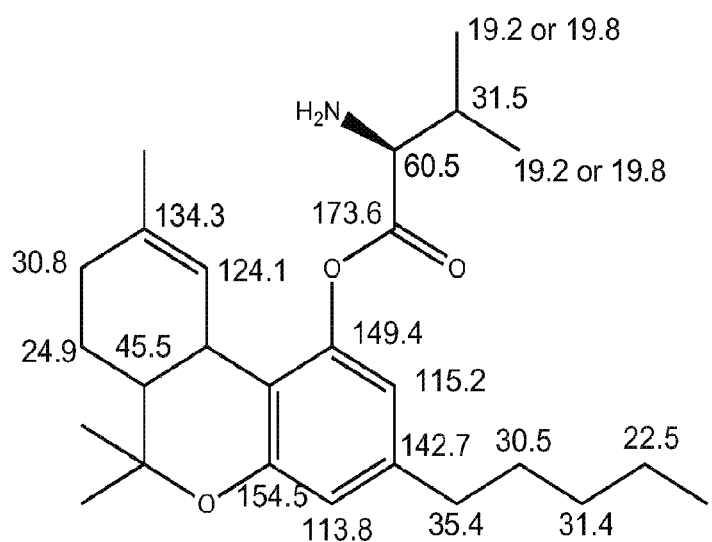
FIG. 3: Representative peaks in carbon spectroscopy for compound 6

The latter was dissolved in dichloromethane and 0.05 mmol of tetrakis(triphenylphosphine) palladium was added along with 0.01 mmol of phenyl silane. The reaction was allowed to stir at room temperature for 30 minutes. The solvent was then evaporated and the product 6 was purified using column chromatography (>87% yield) and confirmed by mass spectroscopy in the positive ionization mode (M+H=414.5) (FIG. 2). The structure of product 6 was also confirmed by spectral analysis $^1$H-NMR and $^{13}$C-NMR (see FIG. 3 for $^{13}$C-NMR assignments).

Figure 4:
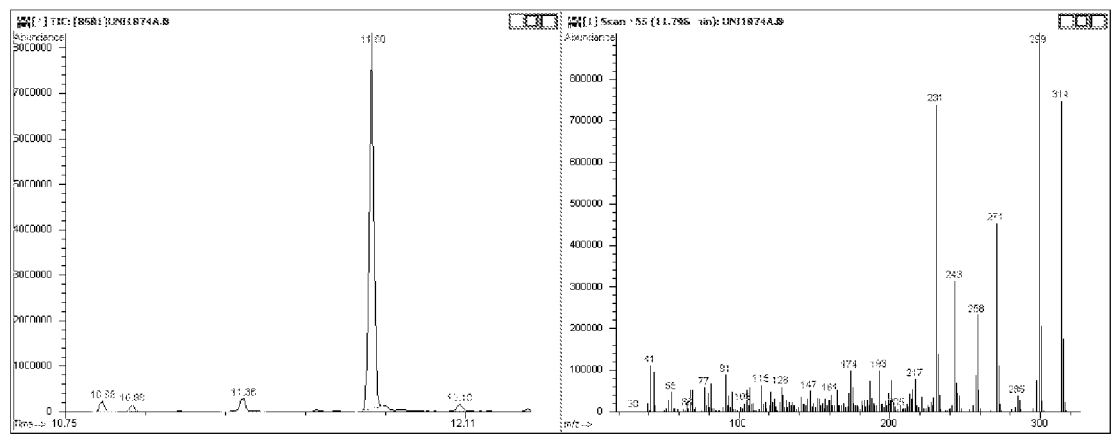
FIG. 4: GC/MS analysis of the hydrolysis product of 6 confirming a $\Delta^9$-THC derivative.

For confirmation that the product 6 is the derivative of $\Delta^9$-THC and not converted to $\Delta^8$-THC, compound 6 was base hydrolyzed followed by GC/MS analysis of the hydrolysis product. The analysis confirmed that it is pure $\Delta^9$-THC as shown in FIG. 4.

Example 2

Preparation of $\Delta^9$-THC-sarcosinate (7)

Figure 5:
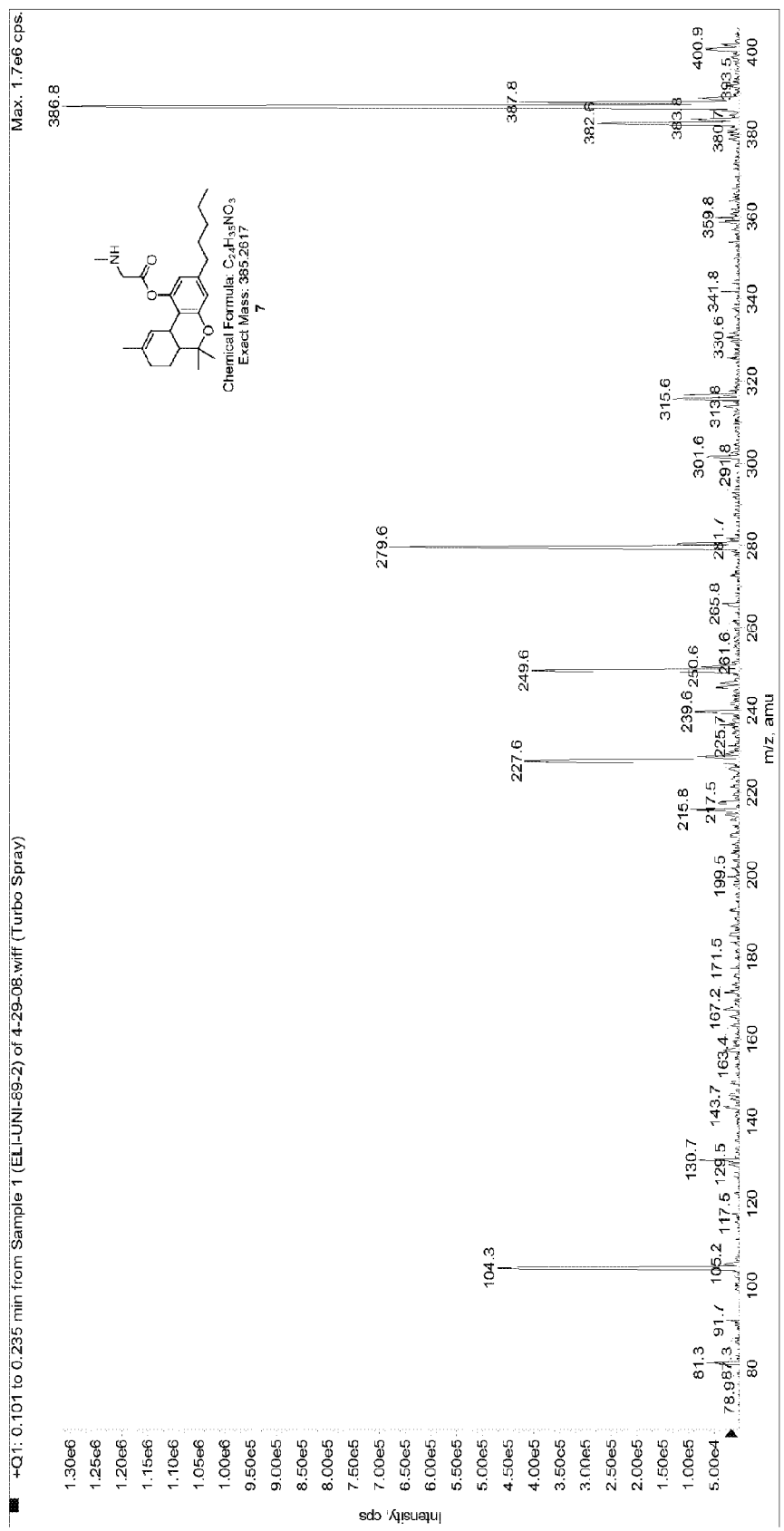
FIG. 5: LC/MS of compound 7 (+ive mode) M+H=386

Following the general procedure outlined in Scheme I, where compound 1 is sarcosine, $\Delta^9$-THC-sarcosinate 7 was synthesized. Product 7 was purified using column chromatography (>80% yield) and confirmed by mass spectroscopy in the positive ionization mode (M+H=386) (FIG. 5). The structure of product 7 was also confirmed by spectral analysis $^1$H-NMR and $^{13}$C-NMR.

Example 3

Preparation of $\Delta^9$-THC-leucinate (8)

Figure 6:
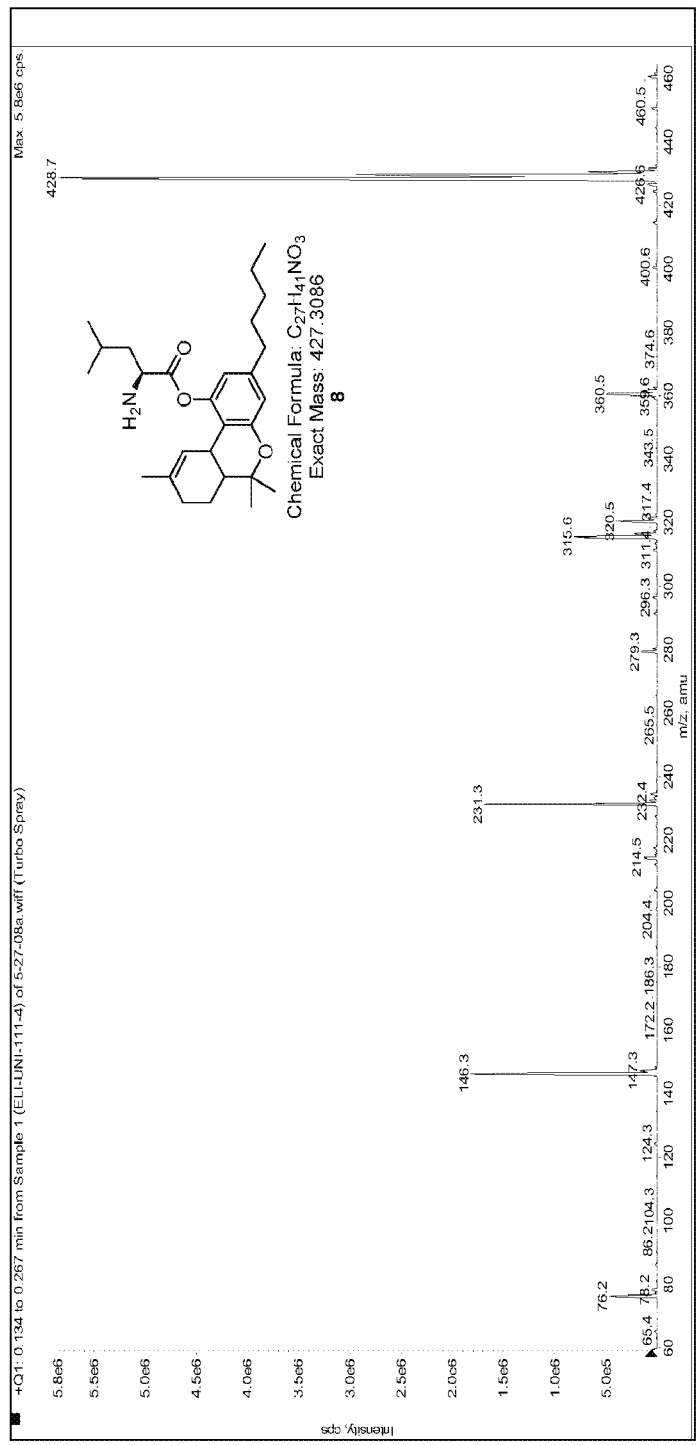
FIG. 6: LC/MS of compound 8 (+ive mode) M+H=428

Following the general procedure outlined in Scheme I, where compound 1 is leucinine, $\Delta^9$-THC-leucinate 8 was synthesized. Product 8 was purified using column chromatography (>81% yield) and confirmed by mass spectroscopy in the positive ionization mode (M+H=428) (FIG. 6). The structure of product 6 was also confirmed by spectral analysis $^1$H-NMR and $^{13}$C-NMR.

Example 4

Preparation of $\Delta^9$-THC-glutaminate (9)

Figure 7:
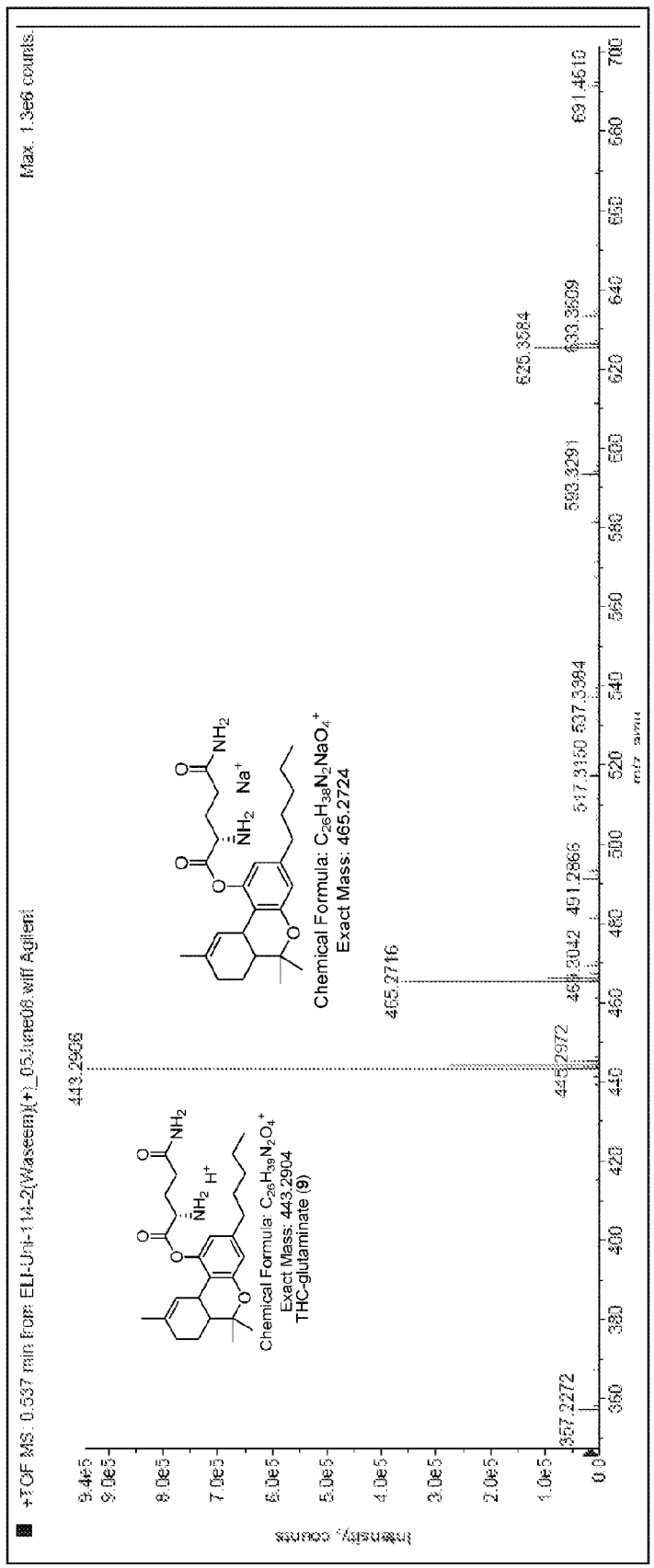
FIG. 7 HREIMS of compound 9 (+ive mode) M+H=443.29 and M+Na=465.27
Figure 8:
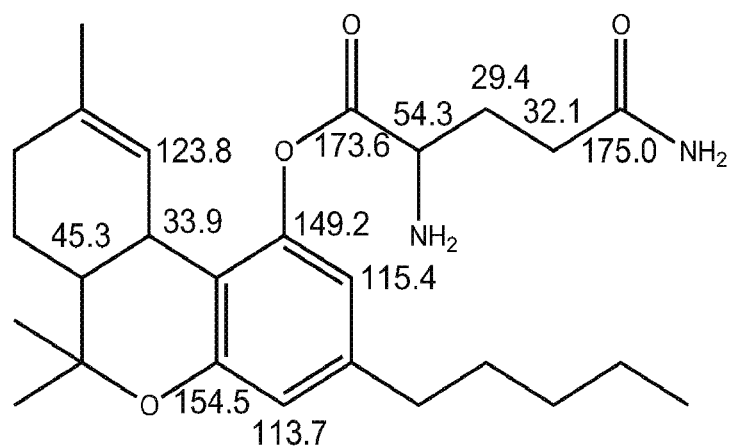
FIG. 8: Representative peaks in carbon spectroscopy for compound 9

Following the general procedure outlined in Scheme I, where compound 1 is glutamine, $\Delta^9$-THC-glutaminate 9 was synthesized. Product 9 was purified using column chromatography (>85% yield) and confirmed by mass spectroscopy in the positive ionization mode (M+H=443) (FIG. 7). The structure of product 9 was also confirmed by spectral analysis ($^1$H-NMR and $^{13}$C-NMR (see FIG. 8 for $^{13}$C-NMR assignments).

Example 5

Preparation of $\Delta^9$-THC-tryptophinate (10)

Figure 9:
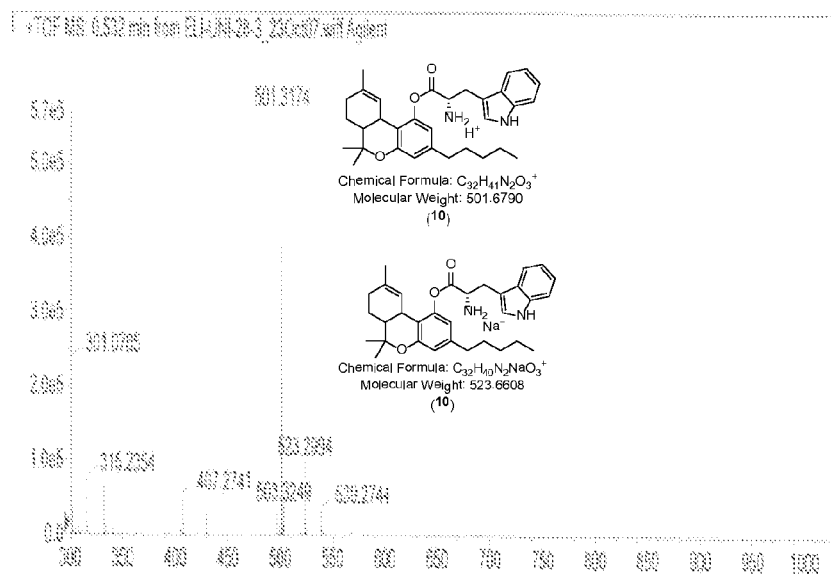
FIG. 9: HREIMS of compound 10 (+ive mode) M+H=501.6, M+Na=523.6 and M+K=539.3
Figure 10:
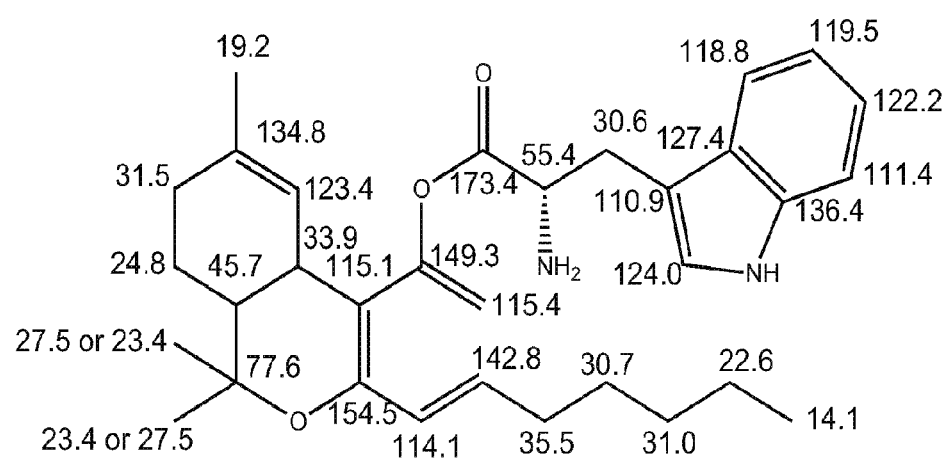
FIG. 10: Representative peaks in carbon spectroscopy for compound 10

Following the general procedure outlined in Scheme I, where compound 1 is tryptophan, $\Delta^9$-THC-tryptophinate 10 was synthesized. Product 10 was purified using column chromatography (>86% yield) and confirmed by mass spectroscopy in the positive ionization mode (M+H=501) (FIG. 9). The structure of product 10 was also confirmed by spectral analysis $^1$H-NMR and $^{13}$C-NMR (see FIG. 10 for $^{13}$C-NMR assignments).

Example 6

Preparation of Δ⁹-THC-tyrosinate (11)

Figure 11:
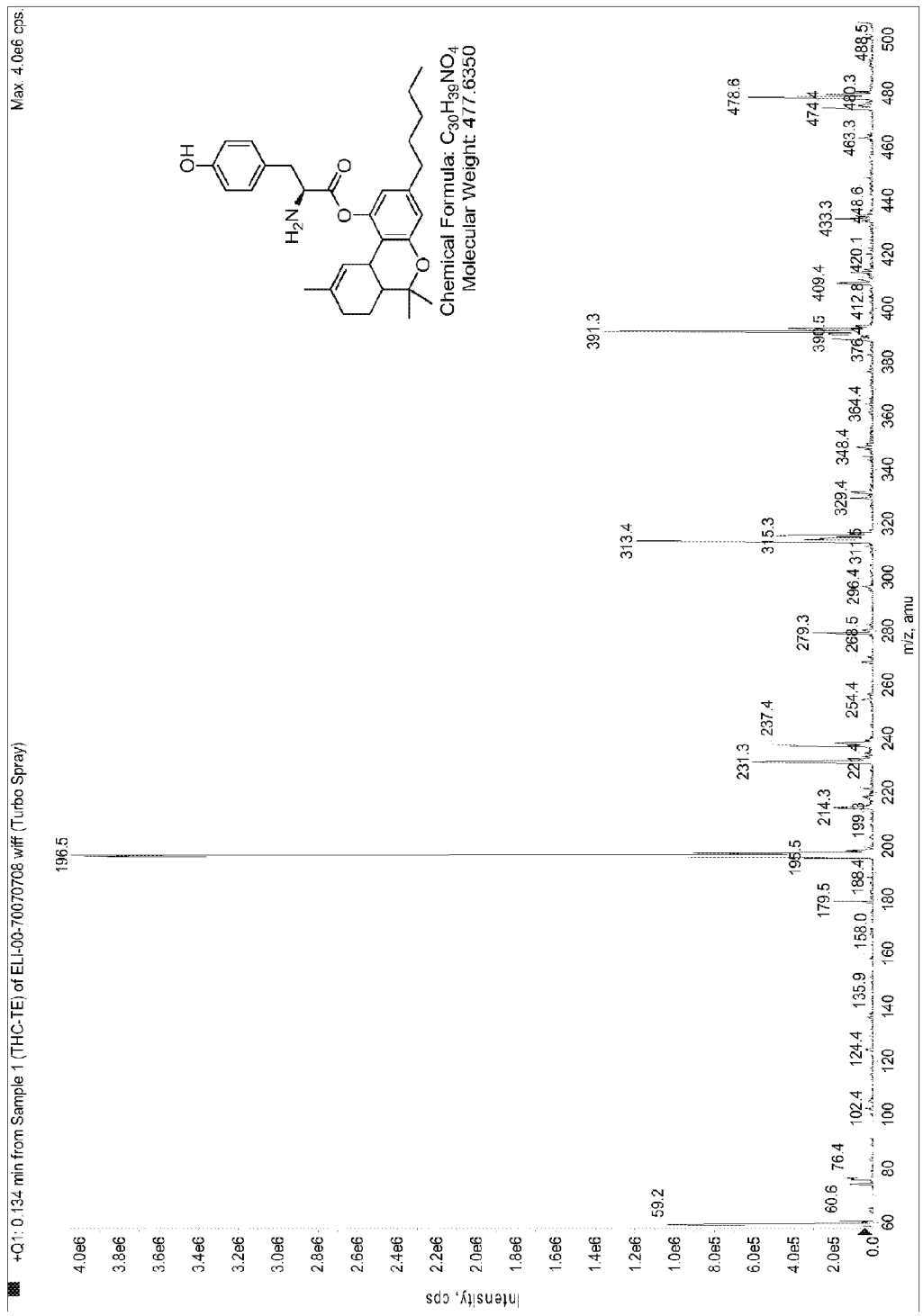
FIG. 11: LC/MS of compound II (+ive mode) M+H=478.3

Following the general procedure outlined in Scheme I, where compound 1 is tyrosine, Δ⁹-THC-tyrosinate 11 was synthesized. Product 11 was purified using column chromatography (>82% yield) and confirmed by mass spectroscopy in the positive ionization mode (M+H=478.3) (FIG. 11). The structure of product 10 was also confirmed by spectral analysis ¹H-NMR and ¹³C-NMR.

Example 7

Preparation of Δ⁹-THC-β-alaninate (12)

Figure 12:
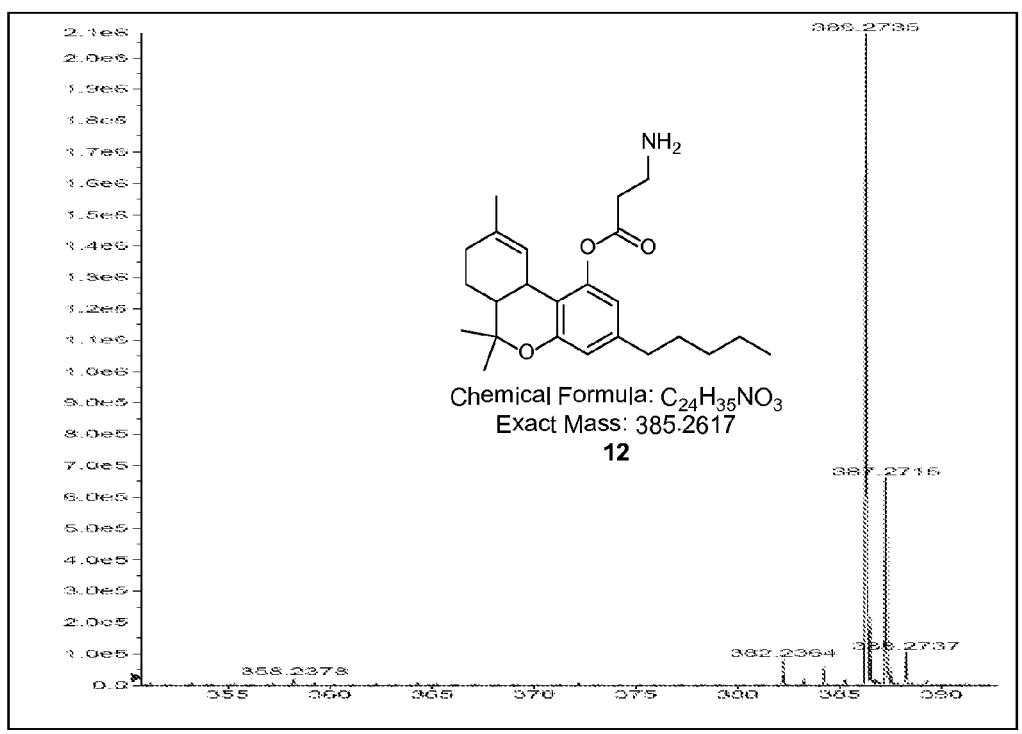
FIG. 12: HREIMS of compound 12 (+ve mode) M+H=

Following the general procedure outlined in Scheme I, where compound 1 is B-alanine, Δ⁹-THC-β-alaninate 12 was synthesized. Product 12 was purified using column chromatography (>82% yield) and confirmed by mass spectroscopy in the positive ionization mode (M+H=386.3) (FIG. 12). The structure of product 6 was also confirmed by spectral analysis ¹H-NMR and ¹³C-NMR.

Example 8

Preparation of Δ⁹-THC-4-(4-aminophenyl)butyrate (12)

Figure 13:
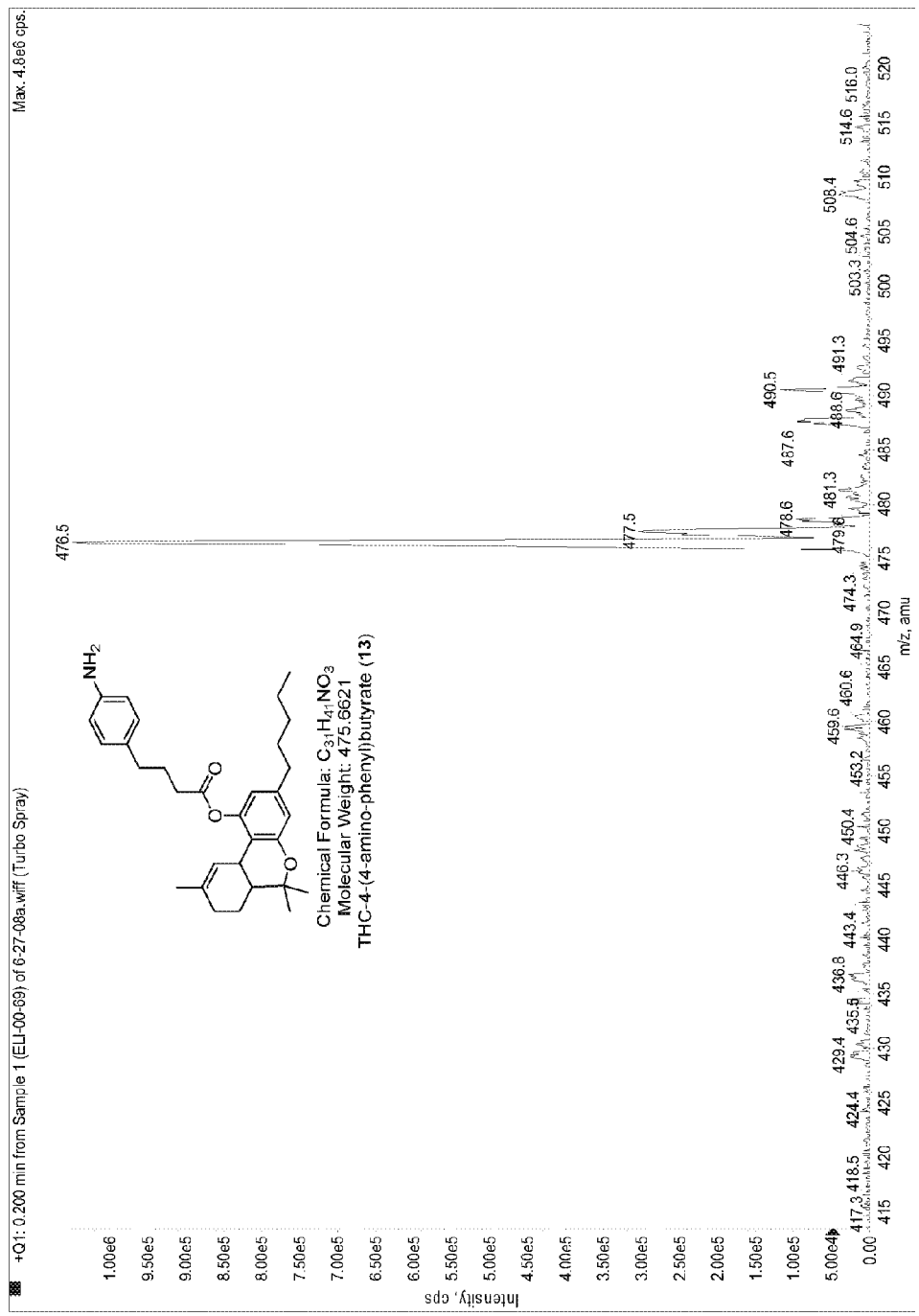
FIG. 13: LCMS of compound 13 (+ive mode) M+H=476
Figure 14:
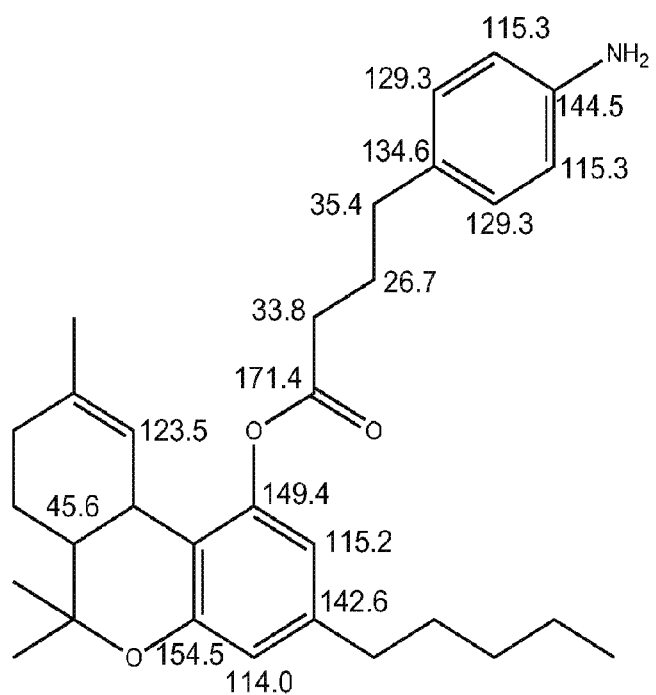
FIG. 14: Representative peaks in carbon spectroscopy for compound 13

Following the general procedure outlined in Scheme I, compound 12 was synthesized, where compound 1 was 4-(4-aminophenyl)butyrate and was used without any protection. Product 12 was purified using column chromatography (>90% yield) and confirmed by mass spectroscopy in the positive ionization mode (M+H=476) (FIG. 13). The structure of product 12 was also confirmed by spectral analysis ¹H-NMR and ¹³C-NMR (see FIG. 14 for ¹³C-NMR assignments).

Scheme II:
Scheme for the preparation of THC hemisuccinate derivatives. Scheme II

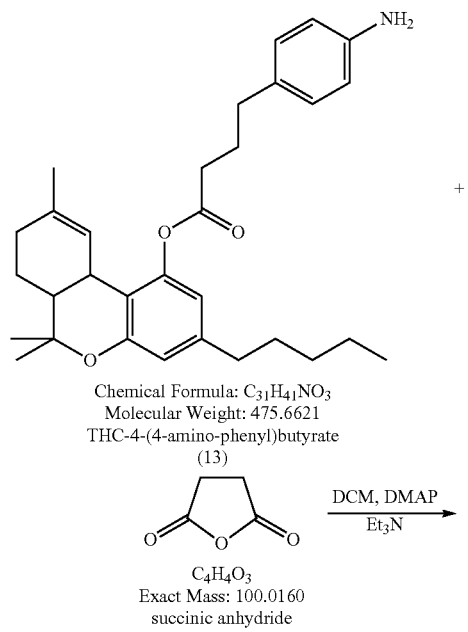

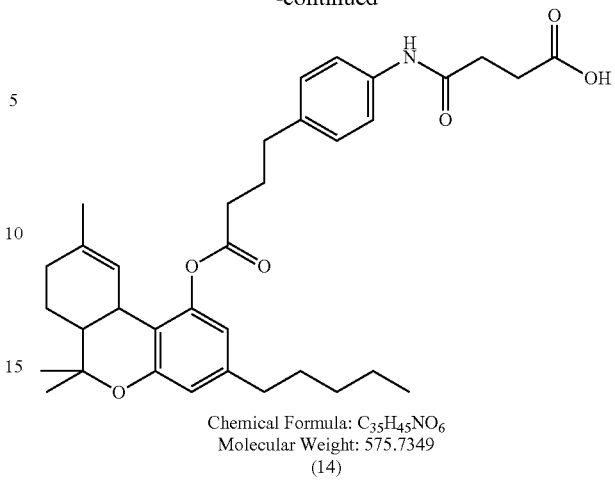

Example 9

Preparation of THC-4(4-aminophenyl)butyrate-hemisuccinate (14)

THC-4(4-aminophenyl)butyrate (13) was dissolved in 50 mL of dichloromethane and 1.1 eq of succinic anhydride was added along with catalytic amount of DMAP (di-methyl amino pyridine). 1.1 eq. of triethyl amine was added drop wise with a syringe and reaction was allowed to run overnight at room temperature.

In the morning, TLC indicated complete conversion of the starting material to product. Solvent was evaporated up to approximately one third of volume on rotavap, and then 1 mL of DCM was added in it.

A column was packed with silica gel (10 eq.) in DCM and the reaction mixture, which was dissolved in DCM, was loaded at the top of the column. Fractions were collected initially in DCM and then increased to 50% EtOAc. Product came in 40% EtOAc in DCM. Fractions containing pure product were combined and the solvent was evaporated to dryness to get the product (14) (95% yield).

Figure 15:
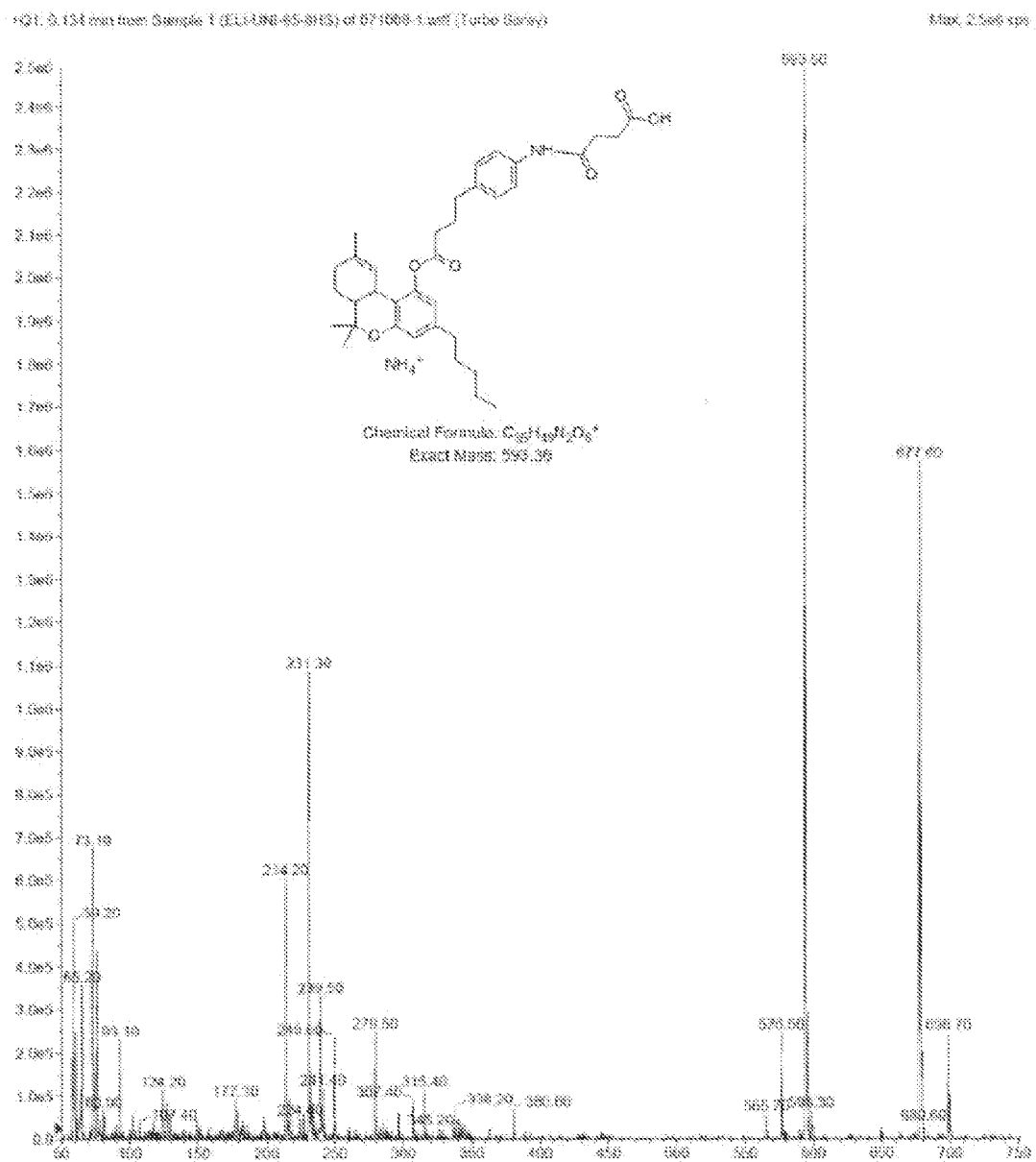
FIG. 15: LCMS of compound 14 (+ive mode) M+NH$_4^+$=593.7
Figure 16:
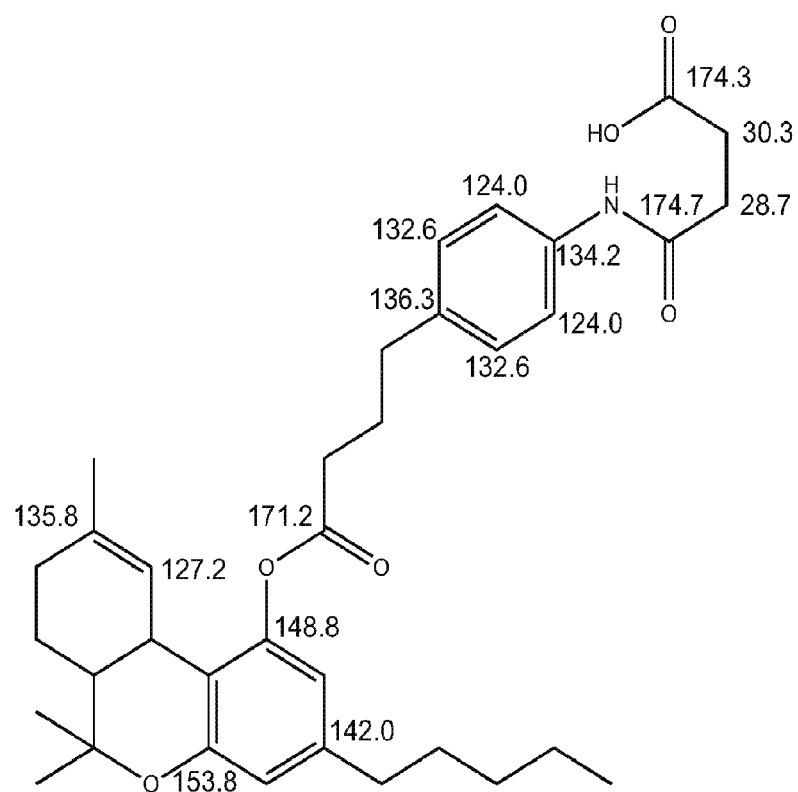
FIG. 16: Representative peaks in carbon spectroscopy for compound 14

Product 14 was confirmed by mass spectroscopy in the positive ionization mode (M+NH₄⁺=593) (FIG. 15). The structure of product 14 was also confirmed by spectral analysis ¹H-NMR and ¹³C-NMR (see FIG. 16 for ¹³C-NMR assignments).

Example 10

Preparation of THC-valinate-hemisuccinate (15)

Figure 17:
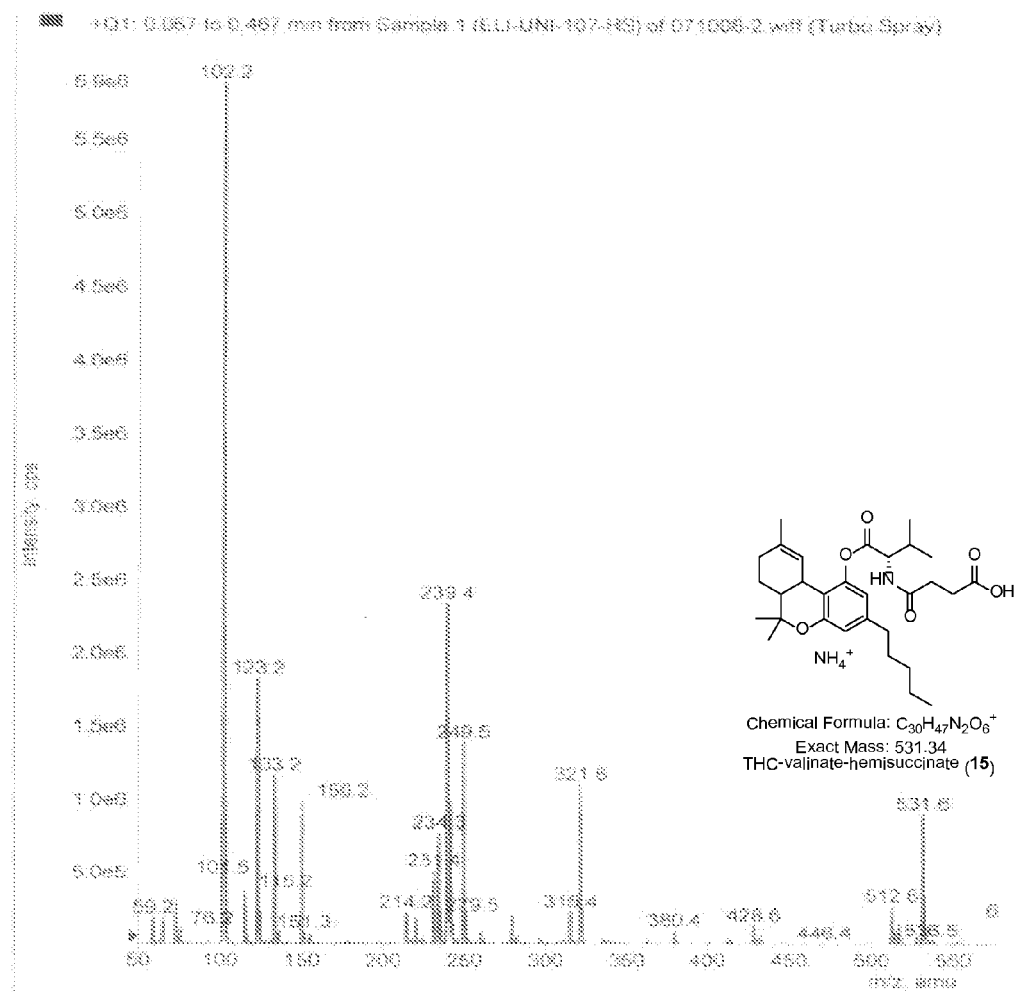
FIG. 17: LCMS of compound 15 (+ive mode) M+NH$_4^+$=531.7
Figure 18:
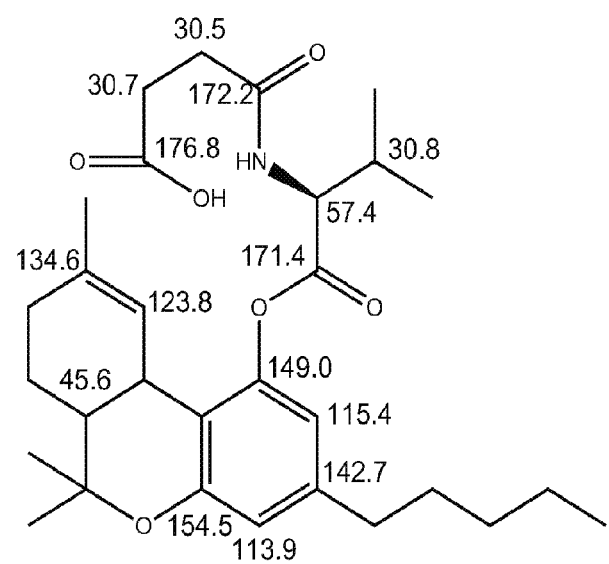
FIG. 18 Representative peaks in carbon spectroscopy for compound 15

Compound 15 was also prepared using scheme II, where the starting material was compound 6 (THC-valinate). Product 15 was purified using column chromatography (>85% yield) and confirmed by mass spectroscopy in the positive ionization mode (M+NH₄⁺=531) (FIG. 17). The structure of product 15 was also confirmed by spectral analysis ¹H-NMR and ¹³C-NMR (see FIG. 18 for ¹³C-NMR assignments).

Spectral analysis of Δ⁹-THC prodrugs prepared above: Identity and purity of the synthesized prodrugs was established by spectral means including ¹H-NMR, ¹³C-NMR and 2D-NMR such as COSY, HMQC, HMBC, as well as other spectroscopic means (IR, UV and MS). The synthetic protocols outlined above yielded prodrugs with ≥95% purity.

Example 11

THC Prodrugs Preformulation Data

A. Solubility
a. Aqueous Solubility (μM)

| pH | THC | THC-Sarcosine | THC-Valine | THC-Valine malonate | THC-Valine-HS | THC-Leucine |
|---|---|---|---|---|---|---|
| 1.2 | — | 263.16 ± 75.84 | 78.23 ± 0.66 | 103.61 ± 2.11 | 0.12 ± 0.06 | 21.89 ± 0.26 |
| 2 | 0.95 | 393.89 ± 24.21 | 147.35 ± 24.90 | 228.78 ± 9.79 | 0.17 ± 0.06 | 55.46 ± 0.93 |
| 3 | 2.23 | 250.54 ± 7.38 | 69.78 ± 0.33 | 96.65 ± 3.49 | 0.00 | 12.08 ± 1.40 |
| 4 | 1.27 | 131.70 ± 5.13 | 24.10 ± 1.28 | 26.88 ± 3.01 | 0.00 | 4.33 ± 0.20 |
| 5 | 2.23 | 18.54 ± 1.87 | 3.51 ± 0.62 | 2.36 ± 0.01 | 0.67 ± 0.04 | 0.54 ± 0.06 |
| 6 | 2.23 | 1.38 ± 0.18 | 0.17 ± 0.00 | 0.25 ± 0.04 | 24.80 ± 3.51 | 0.19 ± 0.02 |
| 7 | 2.23 | 0.00 ± 0.00 | 0.00 ± 0.00 | 0.11 ± 0.03 | 303.06 ± 60.72 | 0.00 ± 0.00 |
| 8 | 2.23 | 0.00 ± 0.00 | 0.00 ± 0.00 | 0.12 ± 0.01 | 227.86 ± 21.24 | 0.00 ± 0.00 |
| 9 | — | 0.00 ± 0.00 | 0.00 ± 0.00 | 0.27 ± 0.03 | 0.05 ± 0.00 | 0.00 ± 0.00 |
| Water | 2.23 | 0.00 ± 0.00 | 0.00 ± 0.00 | 2.33 ± 1.19 | 16.54 ± 11.69 | 0.00 ± 0.00 |

| pH | THC-Glutamine | THC-Tyrosine | THC-Tryptophan | THC-Tryptophan Malonate | THC-APB-HS |
|---|---|---|---|---|---|
| 1.2 | 134.25 ± 0.05 | 87.76 ± 4.48 | — | 0.95 ± 0.12 | 0 |
| 2 | 367.06 ± 32.44 | 33.00 ± 1.38 | 0 | 2.81 ± 0.19 | 0 |
| 3 | 104.36 ± 2.55 | 11.06 ± 3.73 | — | 0 | 0 |
| 4 | 50.13 ± 4.97 | 1.52 ± 0.06 | — | 0 | 0 |
| 5 | 12.99 ± 0.04 | 0 | 0 | 0 | 0 |
| 6 | 4.84 ± 0.72 | 0 | — | 0 | 0 |
| 7 | 1.18 ± 0.14 | 0 | 0 | 0 | 64.66 ± 0.97 |
| 8 | 0.76 ± 0.74 | 0 | — | 0 | 110.20 ± 26.12 |
| 9 | 0.35 ± 0.04 | 0 | 0 | 0 | 41.45 ± 7.59 |
| Water | 3.63 ± 1.72 | 0 | 0 | 8.02 ± 8.90 | 0 | b. Aqueous Solubility (μg/ml)

| pH | THC | THC-Sarcosinate (7) | THC-Valinate (6) | THC-Valinate malonate | THC-Valinate-HS (15) | THC-Leucinate (8) |
|---|---|---|---|---|---|---|
| 1.2 | — | 101.38 ± 29.22 | 32.16 ± 0.27 | 53.63 ± 1.09 | 0.06 ± 0.03 | 9.36 ± 0.11 |
| 2 | 0.95 | 151.75 ± 9.33 | 53.66 ± 10.30 | 118.42 ± 5.07 | 0.09 ± 0.03 | 23.71 ± 0.40 |
| 3 | 2.23 | 96.52 ± 2.84 | 28.76 ± 0.14 | 50.03 ± 1.80 | 0.00 | 5.17 ± 0.60 |
| 4 | 1.27 | 50.74 ± 1.98 | 10.34 ± 0.53 | 13.92 ± 1.56 | 0.00 | 1.95 ± 0.09 |
| 5 | 2.23 | 7.14 ± 0.72 | 1.27 ± 0.25 | 1.22 ± 0.00 | 0.35 ± 0.02 | 0.23 ± 0.03 |
| 6 | 2.23 | 0.53 ± 0.07 | 0.07 ± 0.00 | 0.13 ± 0.02 | 12.74 ± 1.80 | 0.08 ± 0.01 |
| 7 | 2.23 | 0.00 | 0.00 | 0.05 ± 0.02 | 155.67 ± 31.19 | 0.00 |
| 8 | 2.23 | 0.00 | 0.00 | 0.06 ± 0.00 | 117.04 ± 10.91 | 0.00 |
| 9 | — | 0.00 | 0.00 | 0.14 ± 0.02 | 0.02 ± 0.00 | 0.00 |
| H$_2$0 | 2.23 | 0.0 | 0.05 | 1.21 ± 0.61 | 8.50 ± 6.00 | 0.0 |

| pH | THC-Glutaminate (9) | THC-Tyrosinate (11) | THC-Tryptophanate (10) | THC-Tryptophanate Malonate | THC-APB-HS (14) |
|---|---|---|---|---|---|
| 1.2 | 59.55 ± 0.02 | 41.92 ± 2.14 | — | 1.58 ± 0.19 | 0.00 |
| 2 | 162.82 ± 14.39 | 15.76 ± 0.66 | 0.00 | 4.65 ± 0.31 | 0.00 |
| 3 | 46.29 ± 1.13 | 5.28 ± 1.78 | — | 0.00 | 0.00 |
| 4 | 22.24 ± 2.20 | 0.73 ± 0.03 | — | 0.00 | 0.00 |
| 5 | 5.76 ± 0.02 | 0.00 | 0.00 | 0.00 | 0.00 |
| 6 | 2.15 ± 0.32 | 0.00 | — | 0.00 | 0.00 |
| 7 | 0.52 ± 0.06 | 0.00 | 0.00 | 0.00 | 37.22 ± 0.56 |
| 8 | 0.34 ± 0.33 | 0.00 | — | 0.00 | 63.45 ± 15.04 |
| 9 | 0.16 ± 0.02 | 0.00 | 0.00 | 0.00 | 23.86 ± |
| H$_2$0 | 1.61 ± 0.76 | 0.00 | 0.00 | 13.27 ± 14.72 | 0.00 |

B. Chemical Stability pH Dependent at 25° C.

| | | | | First order rate constant ($\times 10^{-3}$ h$^{-1}$) | | | | | |
|---|---|---|---|---|---|---|---|---|---|
| Medium | THC | THC-Sarcosinate (7) | THC-Valinate (6) | THC-Valinate-HS (15) | THC-Leucinate (8) | THC-Glutaminate (9) | THC-Tyrosinate (11) | THC-Tryptophanate (10) | THC-APB-HS (14) |
| Buffer pH 5.0 | 17.00 | 38.35 ± 4.32 | 4.06 ± 0.01 | Stable | 15.94 ± 3.38 | 70.23 ± 0.92 | 6.32 ± 3.14 | 8.29 | 3.68 |
| Buffer pH 7.0 | 9.80 | 605.61 ± 125.14 | 47.13 ± 1.16 | Stable | 85.91 ± 16.83 | 153.42 ± 4.26 | 25.02 ± 0.88 | 38.03 | Stable |
| Buffer pH 9.0 | — | 1209.25 ± 203.05 | 67.64 ± 7.67 | Stable | 119.98 ± 33.51 | 756.35 ± 106.61 | 53.88 ± 11.36 | — | Stable |
| Water | — | 25.45 ± 21.99 | 23.70 ± 0.77 | Stable | 8.51 ± 2.80 | 32.72 ± 15.19 | 9.40 ± 0.88 | — | 4.81 ± 0.81 |

C. Thermal Stability—120° C. for 10 min.

| | Drug | Initial, µg (%) | Drug remaining, µg (%) | Drug loading (%) |
|---|---|---|---|---|
| THC | THC | 1280.70 ± 108.77 (100) | 1214.10 ± 39.12 (95.05 ± 5.05) | 85.38 ± 7.25 |
| | CBN | 56.76 ± 4.86 | 53.85 ± 1.60 | |
| THC-Sarcosinate (7) | THC | 26.68 ± 3.80 | 54.53 ± 3.35 | 79.82 ± 0.85 |
| | CBN | 40.05 ± 3.45 | 33.83 ± 0.97 | |
| | THC-Sarcosinate (7) | 1197.24 ± 12.69 (100) | 841.38 ± 40.18 (70.30 ± 4.10) | |
| THC-Valinate (6) | THC | 61.91 ± 9.49 | 74.35 ± 5.26 | 104.67 ± 2.22 |
| | CBN | 8.27 ± 1.68 | 8.79 ± 2.43 | |
| | THC-Valinate (6) | 1570.09 ± 33.27 (100) | 1440.57 ± 46.34 (91.80 ± 4.90) | |
| THC-Leucinate (8) | THC | −6.13 ± 0.84 | 25.86 ± 0.83 | 103.65 ± 4.12 |
| | CBN | 16.34 ± 0.50 | 20.27 ± 0.43 | |
| | THC-Leucinate (8) | 1554.80 ± 61.76 (100) | 1383.29 ± 40.73 (88.99 ± 0.92) | |
| THC-Tyrosinate (11) | THC | 92.95 ± 3.08 | 123.75 ± 2.69 | 81.51 ± 4.28 |
| | CBN | 35.68 ± 1.16 | 24.42 ± 0.21 | |
| | THC-Tyrosinate (11) | 1222.61 ± 64.25 (100) | 1138.93 ± 60.67 (93.15 ± 0.06) | |
| THC-Tryptophanate (10) | THC | 97.38 ± 6.39 | 96.10 ± 16.64 | 89.84 ± 4.53 |
| | CBN | 25.59 ± 2.26 | 16.63 ± 2.63 | |
| | THC-Tryptophanate (10) | 1347.57 ± 67.93 (100) | 1216.70 ± 32.88 (90.47 ± 7.00) | |
| THC-Valinate-HS (15) | THC | 96.52 ± 3.72 | 80.26 ± 8.59 | 112.21 ± 4.99 |
| | CBN | 0 | 0 | |
| | THC-Valinate-HS (15) | 1411.49 ± 459.10 (100) | 1350.13 ± 387.10 (96.29 ± 3.89) | |
| THC-APB-HS (14) | THC | 0 | 0 | 96.66 ± 2.18 |
| | CBN | 47.63 ± 9.92 | 38.36 ± 9.70 | |
| | THC-APB-HS (14) | 1449.90 ± 32.76 (100) | 1518.84 ± 34.38 (104.81 ± 4.74) | |
| THC-Glutaminate (9) | THC | 0 | 0 | 63.41 ± 2.57 |
| | CBN | 0 | 0 | |
| | THC-Glutaminate (9) | 951.08 ± 38.55 (100) | 721.31 ± 73.76 (75.75 ± 4.69) | |
| | THC | 161.87 ± 3.06 | 189.89 ± 7.16 | |
| | CBN | 32.34 ± 0.69 | 89.43 ± 19.28 | |

D. Bioreversion
a. Plasma Stability

| Drug | Parameters | Porcine Plasma | Rabbit Plasma |
|---|---|---|---|
| THC-Valinate (6) | K ($\times 10^{-2}$ min$^{-1}$) | 91.16 ± 10.91 | 61.94 ± 6.01 |
| | T$_{1/2}$ (min) | 0.766 ± 0.092 | 1.124 ± 0.109 |
| THC-Sarcosinate (7) | K ($\times 10^{-2}$ min$^{-1}$) | 63.16 ± 10.44 | — |
| | T$_{1/2}$ (min) | 1.11 ± 0.18 | — |
| THC-Leucinate (8) | K ($\times 10^{-2}$ min$^{-1}$) | 42.70 ± 3.58 | 33.84 ± 10.92 |
| | T$_{1/2}$ (min) | 1.629 ± 0.137 | 2.160 ± 0.697 |
| THC-Glutaminate (9) | K ($\times 10^{-2}$ min$^{-1}$) | 53.41 ± 5.84 | — |
| | T$_{1/2}$ (min) | 1.31 ± 0.14 | — |
| THC-Tryptophanate (10) | K ($\times 10^{-2}$ min$^{-1}$) | 48.55 ± 5.90 | — |
| | T$_{1/2}$ (min) | 1.44 ± 0.17 | — |
| THC-Tyrosinate (11) | K ($\times 10^{-2}$ min$^{-1}$) | 93.53 ± 8.79 | — |
| | T$_{1/2}$ (min) | 0.74 ± 0.07 | — |
| THC-APB-HS (14) | K ($\times 10^{-2}$ min$^{-1}$) | Stable | — |
| | T$_{1/2}$ (min) | Stable | — |
| THC-Valinate-HS (15) | K ($\times 10^{-2}$ min$^{-1}$) | 85.54 ± 3.74 | — |
| | T$_{1/2}$ (min) | 8.11 ± 0.35 | — | b. Porcine Buccal Tissue Homogenate Stability
Protein Concentration 2 mg/ml

| Drug | Parameters | Porcine Tissue | Control (IPBS) |
|---|---|---|---|
| THC-Valinate (6) | K ($\times 10^{-3}$ min$^{-1}$) | 16 ± 0.19 | 3.66 ± 0.68 |
| | $T_{1/2}$ (min) | 43.30 ± 0.51 | 192.50 ± 35.62 |
| THC-Sarcosinate (7) | K ($\times 10^{-3}$ min$^{-1}$) | 37.36 ± 3.87 | 23.47 ± 1.60 |
| | $T_{1/2}$ (min) | 18.91 ± 0.43 | 29.59 ± 2.01 |
| THC-Leucinate (8) | K ($\times 10^{-3}$ min$^{-1}$) | 22.98 ± 1.49 | 5.49 ± 0.46 |
| | $T_{1/2}$ (min) | 30.21 ± 1.95 | 126.70 ± 10.63 |
| THC-Glutaminate (9) | K ($\times 10^{-3}$ min$^{-1}$) | 40.41 ± 3.30 | 26.30 ± 0.14 |
| | $T_{1/2}$ (min) | 17.21 ± 1.40 | 26.35 ± 0.14 |
| THC-Tryptophanate (10) | K ($\times 10^{-3}$ min$^{-1}$) | 9.06 ± 1.26 | 0.77 ± 0.02 |
| | $T_{1/2}$ (min) | 77.27 ± 10.73 | 903.12 ± 29.55 |
| THC-Tyrosinate (11) | K ($\times 10^{-3}$ min$^{-1}$) | 21.52 ± 0.55 | 1.11 ± 0.04 |
| | $T_{1/2}$ (min) | 32.21 ± 0.81 | 627.59 ± 25.89 |
| THC-Valinate-HS (15) | K ($\times 10^{-3}$ min$^{-1}$) | 2.96 ± 0.19 | 0.40 ± 0.02 |
| | $T_{1/2}$ (min) | 23.43 ± 1.49 | 1663.15 ± 98.62 |

REFERENCES

1. *Marijuana and Medicine: Assessing the Science Base*, ed. J. E. Joy, S. J. Watson, and J. A. Benson, 1999, Washington, D.C.: National Academy Press.
2. Martin, B. R., *The use of cannabinoids in patients with chronic illness*. U.S. Pharmacist, 2002, 1: p. 61-72.
3. ElSolhy, M. A., E. Harland, and C. W. Waller, *Cannabinoids in Glaucoma II: The effect of different cannabinoids on the intraocular pressure of the rabbit*. Carr Eye Res, 1984. 3(6): p. 841-850.
4. El-Mallakh R. S., *Marihuana and migraine*. Headache, 1987. 2(8): p. 442-443.
5. Voile, Z., I. A. Dvilansky, and I. Nathan, *Cannabinoids block release of serotonin from platelets induced by plasma from migraine patients*, Int. J. Clin. Pharmacol, Res., 1985. 5(4): p. 243-246.
6. Maurer, M., et al., *Delta-9-tetrahydrocannabinol shows antispastic and analgesic effects in a single case double-blind trial*. Eur, Arch. Psychiatry Clin. Neurosci., 1990, 240(1): p. 1-4.
7. Perez, J., *Combined cannabinoid therapy via an oromucosal spray*. Drugs Today (Bare), 2006. 42(8): p. 495-503.
8. McLendon, D. M., R. T. Harris, and W. F. Maule, *Suppression of the cardiac conditioned response by delta-9-tetrahydrocannabinol: A comparison with other drugs*. Psychopharmacology, 1976. 50(2): p. 159-163.
9. Perlin, E., et al., *Disposition and bioavailability of various formulations of tetrahydrocannabinol in the Rhesus monkey*. J, Pharm. Sri., 1985. 74: p. 171-174,
10. Ohlsson, A., et al., *Plasma delta-9-tetrahydrocannabinol concentrations and clinical effects after oral and intravenous administration and smoking with erratic bioavailability which is dependent on food intake*. Clin. Pharmacol. Ther., 1980. 28: p. 409-416.
11. Mattes, R. D., et al., *Cannabinoids and Appetite Stimulation*. Pharmacol Biochem Behav, 1994. 49(1): p. 187-195,
12. Brenneisen, R., et al., *The effect of orally and rectally administered delta-9-tetrahydrocannabinol on spasticity: A pilot study with 2 patients*. Inter, J. Clin. Pharmacol. and Therapeutics, 1996, 34(10): p, 446-452.
13. Hazekamp, A., et al., *Evaluation of a vaporizing device (Volcano) for the pulmonary administration of tetrahydrocannabinol*. J Pharm Sci, 2006. 95(6): p. 1308-17.
14. Szezesniak, A. M., et al., *Ocular hypotensive effects of an intratracheally delivered liposomal delta9-tetrahydrocannabinol preparation in rats*. J Ocul Pharmacol Ther, 2006, 22(3): p, 160-7.
15. Harris, A. S., et al., *Effects of concentration and volume on nasal bioavailability and biological response to desmopressin*. J. Pharm. Sci., 1988, 77: p. 337-339.
16. Guy, G. W. and P. J. Robson, *A Phase I, open label, four-way crossover study to compare the pharmacokinetic profiles of a single dose of 20 mg of a cannabis based medicine extract (CBME) administered on 3 different areas of the buccal mucosa and to investigate the pharmacokinetics of CBME per oral in healthy male and female volunteers (GWPK0112)*. Journal of Cannabis Therapeutics, 2003. 3(4): p. 79-120.
17. Cannon, J. B., et al., *Alternate drug delivery routes for A-71623, a potent cholecystokinin-A receptor agonist tetrapeptide*. J, Drug Targeting, 1996. 4: p. 69-78.
18. ElSolhy, M. A., et al., *Rectal bioavailability ref delta-9-tetrahydrocanrtcabinol from various esters*. Pharmacol., Biochem., Behav., 1991. 40: p. 497-502.
19. ElSolhy, M. A., et al., *Rectal bioavailability of delta-9-tetrahydrocannabinol from the hemisuccinate ester in monkeys*. J. Pharm. Sci., 1991. 80(10): p. 942-945.
20, Watanabe, Y., et al., *Pharmacodynamics and pharmacokinetics of recombinant human granulocyte colony-stimulating factor (rhG-CSF) after administration of a rectal dosage vehicle*. Biol. Pharm. 1996. 19: p, 1059-1063.
21. Acarturk. F. and J. R. Robinson, *Vaginal permeability and enzymatic activity studies in normal and ovariectomized rabbits*. Pharm. Res., 1996. 13: p. 779-783.
22. Majumdar, S., S. Duvvuri, and A. K. Mitra, *Membrane transporter/receptor-targeted prodrug design: strategies for human and veterinary drug development*. Adv Drug Deli Rev, 2004, 56(10): p. 1437-52.
23, Majumdar, S. and A. K. Mitra, *Approaches towards enhanced transepithelial drug delivery*. Discov Med, 2006. 6(36): p. 229-33.
24. Majumdar, S. and A. K. Mitra, *Chemical modification and formulation approaches to elevated drug transport across cell membranes*. Expert Opin Drug Deliv, 2006. 3(4): p. 511-27,
25. Soul-Lawton, J., et al., *Absolute bioavailability and metabolic disposition of valaciclovir, the L-valyl ester of acyclovir, following oral administration to humans*, Antimicrob Agents Chemother, 1995. 39(12): p. 2759-64.
26. Anand, B. S., et. al., *Amino acid prodrugs of acyclovir as possible antiviral agents against ocular HSV-1 infections: interactions with the neutral and cationic amino acid transporter on the corneal epithelium*. Curr Eye Res, 2004, 29(2-3): p. 153-66.
27. Anand, B. S., S. Katragadda, and A. K. Mitra, *Pharmacokinetics of novel dipeptide ester prodrugs of acyclovir after oral administration: intestinal absorption and liver metabolism*. J Pharmacol Exp Ther, 2004. 311(2): p, 659-67.
28. Anand, B., Y. Nashed, and A. Mitra, *Novel dipeptide prodrugs of acyclovir for ocular herpes infections: Bioreversion, antiviral activity and transport across rabbit cornea*. Curr Eye Res, 2003, 26(3-4): p. 151-63.
29. Anand, B. S., et al., *In vivo antiviral efficacy of a dipeptide acyclovir prodrug, val-val-acyclovir, against HSV-1 epithelial and stromal keratitis in the rabbit eye model*. Invest Ophthalmol Vis Sci, 2003, 44(6): p. 2529-34.
30. Majumdar, S., V. Kansara, and A. K. Mitra, *Vitreal pharmacokinetics of dipeptide monoester prodrugs of ganciclovir*. J Ocul Pharmacol Ther, 2006. 22(4): p. 231-41.

31. Majumdar, S., et al., *Dipeptide monoester ganciclovir prodrugs for treating HSV-1-induced corneal epithelial and stromal keratitis: in vitro and in vivo evaluations.* J Ocul Pharmacol Ther, 2005. 21(6): p. 463-74.

32. Jain, R., et al., *Evasion of P-gp mediated cellular efflux and permeability enhancement of HIV-protease inhibitor saquinavir by prodrug modification.* Int J Pharm, 2005. 303(1-2): p. 8-19.

33. Jain, R., et al., *Circumventing P-glycoprotein-mediated cellular efflux of quinidine by prodrug derivatianion.* Mol Pharm, 2004. 1(4): p. 290-9.

34. Tanino, T., et al., *Paclixel-2'-Ethylcarbonate prodrug can circumvent P-glycoprotein-mediated cellular efflux to increase drug cytotoxicity.* Pharm Res, 2007. 24(3): p. 555-65.

35. Katragadda, S., R. S. Talluri, and A. K. Mitra, *Modulation of P-glycoprotein-mediated efflux by prodrug derivatization: an approach involving peptide transporter-mediated influx across rabbit cornea.* J Ocul Pharmacol Ther, 2006. 22(2): p, 110-20.

36. Hutchinson, I., et al., *Antitumor benzothiazoles. 16. Synthesis and pharmaceutical properties of antitumor 2-(4-aminophenyl)benzothiazole amino acid prodrugs.* J Med Chem, 2002. 45(3): p. 744-7.

37. Kasai, M., et al., *AS-924, a novel orally active bifunctional prodrug of ceftizoxime. Synthesis and relationship between physicochemical properties and oral absorption.* Chem Pharm Ball (Tokyo), 1999, 47(8): p. 1081-8.

38. Altomare, C., et al., *Highly water-soluble derivatives of the anesthetic agent propofol: in vitro and in vivo evaluation of cyclic amino acid esters.* Eur J Pharm Sci, 2003, 20(1): p. 17-26.

39. Bradshaw, T. D., et al., *In vitro evaluation of amino acid prodrugs of novel antitumour 2-(4-amino-3-methylphenyl)benzothiazoles.* Br J Cancer, 2002. 86(8); p. 1348-54.

40. Taori, A., et al., *Nalidixic acid prodrugs: amides from amino acid ester and nalidixic acid.* Arch. Pharm Res, 1991. 14(1): p. 48-51.

41. Sanchez, J. P., et al., *Quinolone antibacterial agents, Synthesis and structure-activity relationships of a series of amino acid prodrugs of racemic and chiral 7-(3-amino-1-pyrrolidinyl)quinolones. Highly soluble quinolone prodrugs with in vivo pseudomonas activity.* J Med Chem, 1992, 35(10): p. 1764-73.

42. Ohsumi, K., et al., *Synthesis and antitumor activities of amino acid prodrugs of amino-combretastatins.* Anticancer Drug Des, 1999. 14(6): p. 539-48, 43. Feng, X., Y. J. Yuan, and J. C. Wu, *Synthesis and evaluation of water-soluble paclitaxel prodrugs.* Bioorg Med Chem Lett, 2002. 12(22): p. 3301-3, 44. Yamaguchi, T., et al., *Synthesis of taxoids 5. Synthesis and evaluation of novel water-soluble prodrugs of a 3'-desphenyl-3'-cyclopropyl analogue of docetaxel.* Bioorg Med Chem Lett, 1999, 9(12): p. 1039-44.

45. Takata, J., et al., *Vitamin K prodrugs: 1. Synthesis of amino acid esters of menahydroquinone-4 and enzymatic reconversion to an active form.* Pharm Res, 1995. 12(1): p, 18-23, 46. N. H., et al., *Water soluble prodrugs the antitumor agent 3[(3-amino-4-methoxy)phenyl]-2-(3,4,5-trimethoxyphenyl)cyclopent-2-ene-1-one.* Bioorg Med Chem, 2003. 11(6): p. 1021-9

We claim:
1. A $\Delta^9$-THC aminoester composition of the formula

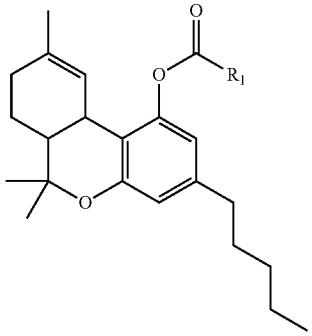

where R1 is natural amino acid residue, and salts thereof; and wherein the $\Delta^9$-THC aminoester composition consists essentially of pure $\Delta^9$-THC amino ester.

2. Method of preparation of the $\Delta^9$-THC aminoester compositions of claim 1 as shown in scheme I comprising the steps of 1) preparing the allyl formate derivative of the amino acid, 2) reacting the allyl formate derivative of the amino acid with $\Delta^9$-THC, 3) deprotecting the $\Delta^9$-THC allyl formate derivative of the amino acid, and 4) preparation of the water soluble salts of the amino acid esters of $\Delta^9$-THC.

3. A method of treating any disease condition responsive to $\Delta^9$-THC comprising administration of at least one $\Delta^9$-THC aminoester composition of claim 1 in a pharmaceutically acceptable carrier using a pharmaceutically acceptable formulation and method of administration.

4. A $\Delta^9$-THC aminoester composition of the formula

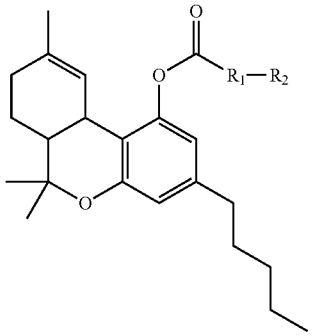

where $R_1$ and $R_2$ are residues of natural amino acids, and salts thereof wherein the $\Delta^9$-THC aminoester composition consists essentially of a pure $\Delta^9$-THC aminoester.

5. Method of preparation of the $\Delta^9$-THC aminoester compositions of claim 4 as shown in scheme I comprising the steps of 1) preparing the allyl formate derivative of the amino acid, 2) reacting the allyl formate derivative of the amino acid with $\Delta^9$-THC, 3) deprotecting the $\Delta^9$-THC allyl formate derivative of the amino acid, 4) reacting the allyl formate derivative of the second amino acid with the $\Delta^9$-THC-amino acid, 5) deprotecting the allyl formate derivative to generate the di-amino acid derivative of $\Delta^9$-THC, and 6) preparation of the water soluble salts of the amino acid esters of $\Delta^9$-THC.

6. A method of treating any disease condition responsive to $\Delta^9$-THC comprising administration of at least one composition of claim 4 in a pharmaceutically acceptable carrier using a pharmaceutically acceptable formulation and method of administration.

7. A $\Delta^9$-THC aminoester composition of the formula

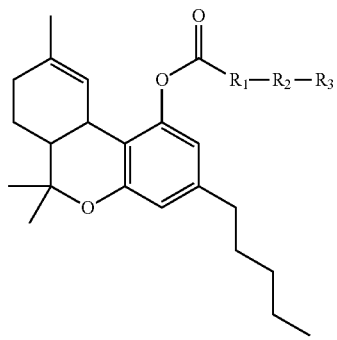

where $R_1$, $R_2$ and $R_3$ are residues of natural acids, and salts thereof; and wherein the $\Delta^9$-THC aminoester composition consists essentially of a pure $\Delta^9$-THC aminoester.

8. Method of preparation of compositions of claim 7 as shown in scheme I comprising the steps of 1) preparing the allyl formate derivative of the amino acid, 2) reacting the allyl formate derivative of the amino acid with $\Delta^9$-THC, 3) deprotecting the $\Delta^9$-THC allyl formate derivative of the amino acid, 4) reacting the allyl formate derivative of the second amino acid with $\Delta^9$-THC-amino acid, 5) deprotecting the $\Delta^9$-THC amino acid coupled with allyl formate derivative of the di-amino acid, 6) reacting the allyl formate derivative of the third amino acid with $\Delta^9$-THC-di-amino acid, 7) deprotecting the allyl formate derivative to generate the triamino acid derivative of $\Delta^9$-THC, and 8) preparation of the water soluble salts of the amino acid esters of $\Delta^9$-THC.

9. A method of treating any disease condition responsive to $\Delta^9$-THC comprising administration of at least one $\Delta^9$-THC aminoester composition of claim 7 in a pharmaceutically acceptable carrier using a pharmaceutically acceptable formulation and method of administration.

10. Compositions containing the hemisuccinate or hemigluturate derivatives of $\Delta^9$-THC aminoester compounds of claim 1.

11. A method of preparing the hemisuccinate and hemigluturate esters of the $\Delta^9$-THC aminoester compounds of claim 1 by reacting the $\Delta^9$-THC aminoester compounds of claim 1 with succinic or glutaric anhydride in the presence of a base catalyst such as a mixture of dimethylaminopyridine and triethylamine followed by the purification of the reaction mixture.

12. A method of treating any disease condition responsive to $\Delta^9$-THC comprising administration of at least one $\Delta^9$-THC aminoester composition of claim 10 in a pharmaceutically acceptable carrier using a pharmaceutically acceptable formulation and method of administration.

13. Compositions containing the hemisuccinate or hemigluturate derivatives of the $\Delta^9$-THC aminoester compounds of claim 4.

14. A method of preparing the hemisuccinate and hemigluturate esters of the $\Delta^9$-THC aminoester compounds of claim 4 by reacting the $\Delta^9$-THC aminoester compounds of claim 4 with succinic or glutaric anhydride in the presence of a base catalyst such as a mixture of dimethylaminopyridine and triethylamine followed by the purification of the reaction mixture.

15. A method of treating any disease condition responsive to $\Delta^9$-THC comprising administration of at least one composition of claim 13 in a pharmaceutically acceptable carrier using a pharmaceutically acceptable formulation and method of administration.

16. Compositions containing the hemisuccinate or hemigluturate derivatives of the $\Delta^9$-THC aminoester compounds of claim 7.

17. A method of preparing the hemisuccinate and hemigluturate esters of the $\Delta^9$-THC aminoester compounds of claim 7 by reacting the compounds of claim 7 with succinic or glutaric anhydride in the presence of a base catalyst such as a mixture of dimethylaminopyridine and triethylamine followed by the purification of the reaction mixture.

18. A method of treating any disease condition responsive to $\Delta^9$-THC comprising administration of at least one composition of claim 16 in a pharmaceutically acceptable carrier using a pharmaceutically acceptable formulation and method of administration.

19. A pharmaceutical composition comprising at least one $\Delta^9$-THC aminoester composition according to claim 1 and a suitable pharmaceutical carrier.

20. A pharmaceutical composition comprising at least one $\Delta^9$-THC aminoester composition according to claim 4 and a suitable pharmaceutical carrier.

21. A pharmaceutical composition comprising at least one $\Delta^9$-THC aminoester composition according to claim 7 and a suitable pharmaceutical carrier.

22. A pharmaceutical composition comprising at least one $\Delta^9$-THC aminoester composition according to claim 10 and a suitable pharmaceutical carrier.

23. A pharmaceutical composition comprising at least one $\Delta^9$-THC aminoester composition according to claim 13 and a suitable pharmaceutical carrier.

24. A pharmaceutical composition comprising at least one $\Delta^9$-THC aminoester composition according to claim 16 and a suitable pharmaceutical carrier.

25. The composition according to claim 1 where $R_1$ is valine, sarcosine, leucine, glutamine, tryptophan, tyrosine, or alanine and salts thereof.

26. The $\Delta^9$-THC aminoester composition according to claim 4, where $R_1$ and $R_2$ are valine, sarcosine, leucine, glutamine, tryptophan, tyrosine, or alanine or a combination thereof, and salts thereof.

27. The $\Delta^9$-THC aminoester composition according to claim 7, where $R_1$, $R_2$ and $R_3$ are valine, sarcosine, leucine, glutamine, tryptophan, tyrosine, or alanine or a combination thereof, and salts thereof.

28. A $\Delta^9$-THC aminoester composition of the formula

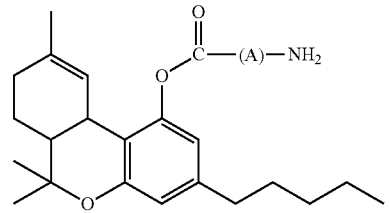

where A is a residue of 1, 2 or 3 natural amino acids, and salts thereof; and wherein the $\Delta^9$-THC aminoester composition consists essentially of a pure $\Delta^9$-THC aminoester.

29. A method of treating a disease condition responsive to THC comprising administration of at least one $\Delta^9$-THC aminoester composition of claim 28 in a pharmaceutically acceptable carrier using a pharmaceutically acceptable formulation and method of administration.

30. The $\Delta^9$-THC aminoester composition according to claim 28, where A is the residue of one natural amino acid and salts thereof.

31. Method of preparation of the compositions of claim 30 as shown in scheme I comprising the steps of 1) preparing the allyl formate derivative of the amino acid, 2) reacting the allyl formate derivative of the amino acid with $\Delta^9$-THC, 3) deprotecting the $\Delta^9$-THC allyl formate derivative of the amino acid, and 4) preparation of the water soluble salts of the amino acid ester of $\Delta^9$-THC.

32. A method of treating a disease condition responsive to $\Delta^9$-THC comprising administration of at least one $\Delta^9$-THC aminoester composition of claim 30 in a pharmaceutically acceptable carrier using a pharmaceutically acceptable formulation and method of administration.

33. The $\Delta^9$-THC aminoester composition according to claim 28, where A is the residue of two natural amino acids and salts thereof.

34. Method of preparation of compositions of the $\Delta^9$-THC aminoester claim 33 as shown in scheme I comprising the steps of 1) preparing the allyl formate derivative of the first amino acid, 2) reacting the allyl formate derivative of the amino acid with $\Delta^9$-THC, 3) deprotecting the $\Delta^9$-THC allyl formate derivative of the first amino acid, 4) reacting the allyl formate derivative of the second amino acid with $\Delta^9$-THC-amino acid, 5) deprotecting the allyl formate derivative to generate the di-amino acid derivative of $\Delta^9$-THC and 6) preparation of the water soluble salt of the amino acid ester of $\Delta^9$-THC.

35. A method of treating any disease condition responsive to $\Delta^9$-THC comprising administration of at least one composition of claim 33 in a pharmaceutically acceptable carrier using a pharmaceutically acceptable formulation and method of administration.

36. The $\Delta^9$-THC aminoester composition according to claim 28, where A is the residue of three natural amino acids and salts thereof.

37. Method of preparation of the compositions of claim 36 as shown in scheme I comprising the steps of 1) preparing the allyl formate derivative of the first amino acid, 2) reacting the allyl formate derivative of the first amino acid with $\Delta^9$-THC, 3) deprotecting the $\Delta^9$-THC allyl formate derivative of the first amino acid, 4) reacting the allyl formate derivative of the second amino acid with $\Delta^9$-THC-amino acid, 5) deprotecting the $\Delta^9$-THC amino acid coupled with allyl formate derivative of the second amino acid, 6) reacting the allyl formate derivative of the third amino acid with $\Delta^9$-THC-di-amino acid, 7) deprotecting the allyl formate derivative to generate the tri-amino acid derivative of $\Delta^9$-THC, and 8) preparation of the water soluble salts of the amino acid ester of $\Delta^9$-THC.

38. A method of treating a disease condition responsive to $\Delta^9$-THC comprising administration of at least one $\Delta^9$-THC aminoester composition of claim 36 in a pharmaceutically acceptable carrier using a pharmaceutically acceptable formulation and method of administration.

39. $\Delta^9$-THC aminoester compositions containing the hemisuccinate or hemigluturate derivatives of the $\Delta^9$-THC aminoester compounds of claim 28.

40. A method of preparing the hemisuccinate and hemigluturate derivatives of the $\Delta^9$-THC aminoester compounds of claim 39 by reacting the $\Delta^9$-THC aminoester compounds of claim 28 with succinic or glutaric anhydride in the presence of a base catalyst such as a mixture of dimethylaminopyridine and triethylamine followed by the purification of the reaction mixture.

41. A method of treating a disease condition responsive to $\Delta^9$-THC comprising administration of at least one composition of claim 39 in a pharmaceutically acceptable carrier using a pharmaceutically acceptable formulation and method of administration.

42. Compositions containing the hemisuccinate or hemigluturate derivatives of the aminoester compounds of claim 30.

43. A method of preparing the hemisuccinate and hemigluturate derivatives of the compounds of claim 30 by reacting the $\Delta^9$-THC aminoester compounds of claim 28 with succinic or glutaric anhydride in the presence of a base catalyst such as a mixture of dimethylaminopyridine and triethylamine followed by the purification of the reaction mixture.

44. A method of treating a disease condition responsive to $\Delta^9$-THC comprising administration of at least one $\Delta^9$-THC aminoester composition of claim 42 in a pharmaceutically acceptable carrier using a pharmaceutically acceptable formulation and method of administration.

45. Compositions containing the hemisuccinate or hemigluturate derivatives of the $\Delta^9$-THC aminoester compounds of claim 33.

46. A method of preparing the hemisuccinate and hemigluturate esters of the $\Delta^9$-THC aminoester compounds of claim 33 by reacting the $\Delta^9$-THC aminoester compounds of claim 33 with succinic or glutaric anhydride in the presence of a base catalyst such as a mixture of dimethylaminopyridine and triethylamine followed by the purification of the reaction mixture.

47. A method of treating any disease condition responsive to $\Delta^9$-THC comprising administration of at least one $\Delta^9$-THC aminoester composition of claim 45 in a pharmaceutically acceptable carrier using a pharmaceutically acceptable formulation and method of administration.

48. Compositions containing the hemisuccinate or hemigluturate derivatives of the $\Delta^9$-THC aminoester compounds of claim 36.

49. A method of preparing the hemisuccinate and hemigluturate esters of the $\Delta^9$-THC aminoester compounds of claim 36 by reacting the $\Delta^9$-THC aminoester compounds of claim 34 with succinic or glutaric anhydride in the presence of a base catalyst such as a mixture of dimethylaminopyridine and triethylamine followed by the purification of the reaction mixture.

50. A method of treating any disease condition responsive to $\Delta^9$-THC comprising administration of at least one composition of claim 48 in a pharmaceutically acceptable carrier using a pharmaceutically acceptable formulation and method of administration.

51. A pharmaceutical composition comprising at least one $\Delta^9$-THC aminoester composition according to claim 28 and a suitable pharmaceutical carrier.

52. A pharmaceutical composition comprising at least one $\Delta^9$-THC aminoester composition according to claim 30 and a suitable pharmaceutical carrier.

53. A pharmaceutical composition comprising at least one $\Delta^9$-THC aminoester composition according to claim 33 and a suitable pharmaceutical carrier.

54. A pharmaceutical composition comprising at least one $\Delta^9$-THC aminoester composition according to claim 36 and a suitable pharmaceutical carrier.

55. A pharmaceutical composition comprising at least one $\Delta^9$-THC aminoester composition according to claim 39 and a suitable pharmaceutical carrier.

56. A pharmaceutical composition comprising at least one $\Delta^9$-THC aminoester composition according to claim 42 and a suitable pharmaceutical carrier.

57. A pharmaceutical composition comprising at least one $\Delta^9$-THC aminoester composition according to claim 45 and a suitable pharmaceutical carrier.

58. A pharmaceutical composition comprising at least one $\Delta^9$-THC aminoester composition according to claim 48 and a suitable pharmaceutical carrier.

59. The $\Delta^9$-THC aminoester composition according to claim 28 where A is valine, sarcosine, leucine, glutamine, tryptophan, tyrosine, or alanine.

60. The $\Delta^9$-THC aminoester composition according to claim 30, where A is valine, sarcosine, leucine, glutamine, tryptophan, tyrosine, or alanine.

61. The $\Delta^9$-THC aminoester composition according to claim 33, where A is valine, sarcosine, leucine, glutamine, tryptophan, tyrosine, or alanine or a combination thereof.

62. The $\Delta^9$-THC aminoester composition according to claim 36 where A is valine, sarcosine, leucine, glutamine, tryptophan, tyrosine, or alanine or a combination thereof.

63. The $\Delta^9$-THC aminoester composition according to claim 39, where A is valine, sarcosine, leucine, glutamine, tryptophan, tyrosine, or alanine or a combination thereof.

64. The $\Delta^9$-THC aminoester composition according to claim 42, where A is valine, sarcosine, leucine, glutamine, tryptophan, tyrosine, or alanine.

65. The $\Delta^9$-THC aminoester composition according to claim 45, where A is valine, sarcosine, leucine, glutamine, tryptophan, tyrosine, or alanine or a combination thereof.

66. The $\Delta^9$-THC aminoester composition according to claim 48, where A is valine, sarcosine, leucine, glutamine, tryptophan, tyrosine, or alanine or a combination thereof.

\* \* \* \* \*